(12) United States Patent
Jaureguiberry et al.

(10) Patent No.: US 10,936,066 B1
(45) Date of Patent: Mar. 2, 2021

(54) SLEEP DETECTION IN A LOCATION SHARING SYSTEM

(71) Applicant: Snap Inc., Santa Monica, CA (US)

(72) Inventors: Xabier Jaureguiberry, Vincennes (FR); Alexy Lean, Grigny (FR); Antoine Martin, Paris (FR); Antoine Sinton, Courteuil (FR)

(73) Assignee: Snap Inc., Santa Monica, CA (US)

( * ) Notice: Subject to any disclaimer, the term of this patent is extended or adjusted under 35 U.S.C. 154(b) by 0 days.

(21) Appl. No.: 16/274,891

(22) Filed: Feb. 13, 2019

(51) Int. Cl.
*G06F 3/01* (2006.01)
*G06F 16/904* (2019.01)
*G06F 16/906* (2019.01)

(52) U.S. Cl.
CPC .............. *G06F 3/015* (2013.01); *G06F 3/017* (2013.01); *G06F 16/904* (2019.01); *G06F 16/906* (2019.01); *G06F 2203/011* (2013.01)

(58) Field of Classification Search
CPC ... G06F 19/3481; G09B 19/00; A61B 5/4815; A61B 10/0012; A61B 5/742; A61M 21/02; G16H 50/20
See application file for complete search history.

(56) References Cited

U.S. PATENT DOCUMENTS

| | | |
|---|---|---|
| 5,880,731 A | 3/1999 | Liles et al. |
| 6,023,270 A | 2/2000 | Brush, II et al. |
| 6,223,165 B1 | 4/2001 | Lauffer |
| 6,772,195 B1 | 8/2004 | Hatlelid et al. |
| 6,842,779 B1 | 1/2005 | Nishizawa |
| 7,342,587 B2 | 3/2008 | Danzig et al. |
| 7,468,729 B1 | 12/2008 | Levinson |
| 7,636,755 B2 | 12/2009 | Blattner et al. |
| 7,639,251 B2 | 12/2009 | Gu et al. |
| 7,775,885 B2 | 8/2010 | Van Luchene et al. |
| 7,859,551 B2 | 12/2010 | Bulman et al. |
| 7,885,931 B2 | 2/2011 | Seo et al. |
| 7,925,703 B2 | 4/2011 | Dinan et al. |
| 8,088,044 B2 | 1/2012 | Tchao et al. |

(Continued)

FOREIGN PATENT DOCUMENTS

| | | |
|---|---|---|
| CN | 109863532 A | 6/2019 |
| CN | 110168478 A | 8/2019 |

(Continued)

*Primary Examiner* — Toan H Vu
(74) *Attorney, Agent, or Firm* — Schwegman Lundberg & Woessner, P.A.

(57) ABSTRACT

Methods, systems, and devices for predicting a state of a user (e.g., asleep or awake). In some embodiments, the location sharing system accesses historical activity data of the user and extracts historical sleep records from the historical activity data. The system clusters the historical sleep records into a plurality of clusters and extracts a sleep pattern from each one of the plurality of clusters. Then, when the location sharing system receives current activity data of the user, the system can predict whether the user is currently asleep based on the current activity of the user and at least one of the sleep patterns. Some embodiments additionally compute an estimated wake up time of the user. Some embodiments share the predicted physiological state of the user with the user's friends via the map GUI. Some embodiments additionally share the estimated wake up time of the user.

20 Claims, 13 Drawing Sheets

(56) References Cited

U.S. PATENT DOCUMENTS

| | | | |
|---|---|---|---|
| 8,095,878 B2 | 1/2012 | Bates et al. |
| 8,108,774 B2 | 1/2012 | Finn et al. |
| 8,117,281 B2 | 2/2012 | Robinson et al. |
| 8,130,219 B2 | 3/2012 | Fleury et al. |
| 8,146,005 B2 | 3/2012 | Jones et al. |
| 8,151,191 B2 | 4/2012 | Nicol |
| 8,384,719 B2 | 2/2013 | Reville et al. |
| RE44,054 E | 3/2013 | Kim |
| 8,396,708 B2 | 3/2013 | Park et al. |
| 8,425,322 B2 | 4/2013 | Gillo et al. |
| 8,458,601 B2 | 6/2013 | Castelli et al. |
| 8,462,198 B2 | 6/2013 | Lin et al. |
| 8,484,158 B2 | 7/2013 | Deluca et al. |
| 8,495,503 B2 | 7/2013 | Brown et al. |
| 8,495,505 B2 | 7/2013 | Smith et al. |
| 8,504,926 B2 | 8/2013 | Wolf |
| 8,559,980 B2 | 10/2013 | Pujol |
| 8,564,621 B2 | 10/2013 | Branson et al. |
| 8,564,710 B2 | 10/2013 | Nonaka et al. |
| 8,581,911 B2 | 11/2013 | Becker et al. |
| 8,597,121 B2 | 12/2013 | del Valle |
| 8,601,051 B2 | 12/2013 | Wang |
| 8,601,379 B2 | 12/2013 | Marks et al. |
| 8,632,408 B2 | 1/2014 | Gillo et al. |
| 8,648,865 B2 | 2/2014 | Dawson et al. |
| 8,659,548 B2 | 2/2014 | Hildreth |
| 8,683,354 B2 | 3/2014 | Khandelwal et al. |
| 8,692,830 B2 | 4/2014 | Nelson et al. |
| 8,810,513 B2 | 8/2014 | Ptucha et al. |
| 8,812,171 B2 | 8/2014 | Filev et al. |
| 8,832,201 B2 | 9/2014 | Wall |
| 8,832,552 B2 | 9/2014 | Arrasvuori et al. |
| 8,839,327 B2 | 9/2014 | Amento et al. |
| 8,890,926 B2 | 11/2014 | Tandon et al. |
| 8,892,999 B2 | 11/2014 | Nims et al. |
| 8,924,250 B2 | 12/2014 | Bates et al. |
| 8,963,926 B2 | 2/2015 | Brown et al. |
| 8,989,786 B2 | 3/2015 | Feghali |
| 9,086,776 B2 | 7/2015 | Ye et al. |
| 9,105,014 B2 | 8/2015 | Collet et al. |
| 9,241,184 B2 | 1/2016 | Weerasinghe |
| 9,256,860 B2 | 2/2016 | Herger et al. |
| 9,298,257 B2 | 3/2016 | Hwang et al. |
| 9,314,692 B2 | 4/2016 | Konoplev et al. |
| 9,330,483 B2 | 5/2016 | Du et al. |
| 9,357,174 B2 | 5/2016 | Li et al. |
| 9,361,510 B2 | 6/2016 | Yao et al. |
| 9,378,576 B2 | 6/2016 | Bouaziz et al. |
| 9,402,057 B2 | 7/2016 | Kaytaz et al. |
| 9,412,192 B2 | 8/2016 | Mandel et al. |
| 9,460,541 B2 | 10/2016 | Li et al. |
| 9,489,760 B2 | 11/2016 | Li et al. |
| 9,503,845 B2 | 11/2016 | Vincent |
| 9,508,197 B2 | 11/2016 | Quinn et al. |
| 9,544,257 B2 | 1/2017 | Ogundokun et al. |
| 9,576,400 B2 | 2/2017 | Van Os et al. |
| 9,589,357 B2 | 3/2017 | Li et al. |
| 9,592,449 B2 | 3/2017 | Barbalet et al. |
| 9,648,376 B2 | 5/2017 | Chang et al. |
| 9,697,635 B2 | 7/2017 | Quinn et al. |
| 9,706,040 B2 | 7/2017 | Kadirvel et al. |
| 9,744,466 B2 | 8/2017 | Fujioka |
| 9,746,990 B2 | 8/2017 | Anderson et al. |
| 9,749,270 B2 | 8/2017 | Collet et al. |
| 9,792,714 B2 | 10/2017 | Li et al. |
| 9,839,844 B2 | 12/2017 | Dunstan et al. |
| 9,883,838 B2 | 2/2018 | Kaleal, III et al. |
| 9,898,849 B2 | 2/2018 | Du et al. |
| 9,911,073 B1 | 3/2018 | Spiegel et al. |
| 9,936,165 B2 | 4/2018 | Li et al. |
| 9,959,037 B2 | 5/2018 | Chaudhri et al. |
| 9,980,100 B1 | 5/2018 | Charlton et al. |
| 9,990,373 B2 | 6/2018 | Fortkort |
| 10,039,988 B2 | 8/2018 | Lobb et al. |
| 10,097,492 B2 | 10/2018 | Tsuda et al. |
| 10,116,598 B2 | 10/2018 | Tucker et al. |
| 10,155,168 B2 | 12/2018 | Blackstock et al. |
| 10,242,477 B1 | 3/2019 | Charlton et al. |
| 10,242,503 B2 | 3/2019 | McPhee et al. |
| 10,262,250 B1 | 4/2019 | Spiegel et al. |
| 10,362,219 B2 | 7/2019 | Wilson et al. |
| 10,475,225 B2 | 11/2019 | Park et al. |
| 10,504,266 B2 | 12/2019 | Blattner et al. |
| 10,573,048 B2 | 2/2020 | Ni et al. |
| 10,657,701 B2 | 5/2020 | Osman et al. |
| 2002/0067362 A1 | 6/2002 | Nocera et al. |
| 2002/0169644 A1 | 11/2002 | Greene |
| 2005/0162419 A1 | 7/2005 | Kim et al. |
| 2005/0206610 A1 | 9/2005 | Cordelli |
| 2006/0294465 A1 | 12/2006 | Ronen et al. |
| 2007/0113181 A1 | 5/2007 | Blattner et al. |
| 2007/0168863 A1 | 7/2007 | Blattner et al. |
| 2007/0176921 A1 | 8/2007 | Iwasaki et al. |
| 2008/0158222 A1 | 7/2008 | Li et al. |
| 2009/0016617 A1 | 1/2009 | Bregman-amitai et al. |
| 2009/0055484 A1 | 2/2009 | Vuong et al. |
| 2009/0070688 A1 | 3/2009 | Gyorfi et al. |
| 2009/0099925 A1 | 4/2009 | Mehta et al. |
| 2009/0106672 A1 | 4/2009 | Burstrom |
| 2009/0158170 A1 | 6/2009 | Narayanan et al. |
| 2009/0177976 A1 | 7/2009 | Bokor et al. |
| 2009/0202114 A1 | 8/2009 | Morin et al. |
| 2009/0265604 A1 | 10/2009 | Howard et al. |
| 2009/0300525 A1 | 12/2009 | Jolliff et al. |
| 2009/0303984 A1 | 12/2009 | Clark et al. |
| 2010/0011422 A1 | 1/2010 | Mason et al. |
| 2010/0023885 A1 | 1/2010 | Reville et al. |
| 2010/0115426 A1 | 5/2010 | Liu et al. |
| 2010/0162149 A1 | 6/2010 | Sheleheda et al. |
| 2010/0203968 A1 | 8/2010 | Gill et al. |
| 2010/0227682 A1 | 9/2010 | Reville et al. |
| 2011/0093780 A1 | 4/2011 | Dunn |
| 2011/0115798 A1 | 5/2011 | Nayar et al. |
| 2011/0148864 A1 | 6/2011 | Lee et al. |
| 2011/0239136 A1 | 9/2011 | Goldman et al. |
| 2012/0092171 A1* | 4/2012 | Hwang ............... G06F 19/3481 340/575 |
| 2012/0113106 A1 | 5/2012 | Choi et al. |
| 2012/0124458 A1 | 5/2012 | Cruzada |
| 2012/0130717 A1 | 5/2012 | Xu et al. |
| 2013/0103760 A1 | 4/2013 | Golding et al. |
| 2013/0201187 A1 | 8/2013 | Tong et al. |
| 2013/0249948 A1 | 9/2013 | Reitan |
| 2013/0257877 A1 | 10/2013 | Davis |
| 2014/0043329 A1 | 2/2014 | Wang et al. |
| 2014/0055554 A1 | 2/2014 | Du et al. |
| 2014/0057232 A1* | 2/2014 | Wetmore ............... G09B 19/00 434/236 |
| 2014/0125678 A1 | 5/2014 | Wang et al. |
| 2014/0129343 A1 | 5/2014 | Finster et al. |
| 2015/0206349 A1 | 7/2015 | Rosenthal et al. |
| 2015/0238137 A1* | 8/2015 | Eyal ..................... A61B 5/4815 600/508 |
| 2016/0058429 A1* | 3/2016 | Shinar ................ A61B 10/0012 600/551 |
| 2016/0134840 A1 | 5/2016 | Mcculloch |
| 2016/0151603 A1* | 6/2016 | Shouldice ............. A61M 21/02 600/28 |
| 2016/0234149 A1 | 8/2016 | Tsuda et al. |
| 2016/0270718 A1* | 9/2016 | Heneghan ............. G16H 50/20 |
| 2017/0080346 A1 | 3/2017 | Abbas |
| 2017/0087473 A1 | 3/2017 | Siegel et al. |
| 2017/0113140 A1 | 4/2017 | Blackstock et al. |
| 2017/0118145 A1 | 4/2017 | Aittoniemi et al. |
| 2017/0199855 A1 | 7/2017 | Fishbeck |
| 2017/0235848 A1 | 8/2017 | Van Dusen et al. |
| 2017/0310934 A1 | 10/2017 | Du et al. |
| 2017/0312634 A1 | 11/2017 | Ledoux et al. |
| 2018/0047200 A1 | 2/2018 | O'hara et al. |
| 2018/0113587 A1 | 4/2018 | Allen et al. |
| 2018/0115503 A1 | 4/2018 | Baldwin et al. |
| 2018/0315076 A1 | 11/2018 | Andreou |
| 2018/0315133 A1 | 11/2018 | Brody et al. |
| 2018/0315134 A1 | 11/2018 | Amitay et al. |

(56) References Cited

U.S. PATENT DOCUMENTS

| | | | |
|---|---|---|---|
| 2019/0001223 A1 | 1/2019 | Blackstock et al. | |
| 2019/0057616 A1 | 2/2019 | Cohen et al. | |
| 2019/0188920 A1 | 6/2019 | Mcphee et al. | |
| 2019/0251858 A1* | 8/2019 | Baharav | A61B 5/742 |

FOREIGN PATENT DOCUMENTS

| | | | |
|---|---|---|---|
| EP | 2184092 A2 | 5/2010 | |
| JP | 2001230801 A | 8/2001 | |
| JP | 5497931 B2 | 3/2014 | |
| KR | 101445263 B1 | 9/2014 | |
| WO | WO-2003094072 A1 | 11/2003 | |
| WO | WO-2004095308 A1 | 11/2004 | |
| WO | WO-2006107182 A1 | 10/2006 | |
| WO | WO-2007134402 A1 | 11/2007 | |
| WO | WO-2012139276 A1 | 10/2012 | |
| WO | WO-2013027893 A1 | 2/2013 | |
| WO | WO-2013152454 A1 | 10/2013 | |
| WO | WO-2013166588 A1 | 11/2013 | |
| WO | WO-2014031899 A1 | 2/2014 | |
| WO | WO-2014194439 A1 | 12/2014 | |
| WO | WO-2016090605 A1 | 6/2016 | |
| WO | WO-2018081013 A1 | 5/2018 | |
| WO | WO-2018102562 A1 | 6/2018 | |
| WO | WO-2018129531 A1 | 7/2018 | |
| WO | WO-2019089613 A1 | 5/2019 | |

* cited by examiner

SLEEP DETECTION IN A LOCATION SHARING SYSTEM

BACKGROUND

The popularity of electronic messaging, particularly instant messaging, continues to grow. Users increasingly share media content items such as electronic images and videos with each other, reflecting a global demand to communicate more visually. Similarly, users increasingly seek to customize the media content items they share with others, providing challenges to social networking systems seeking to generate custom media content for their members. Embodiments of the present disclosure address these and other issues.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
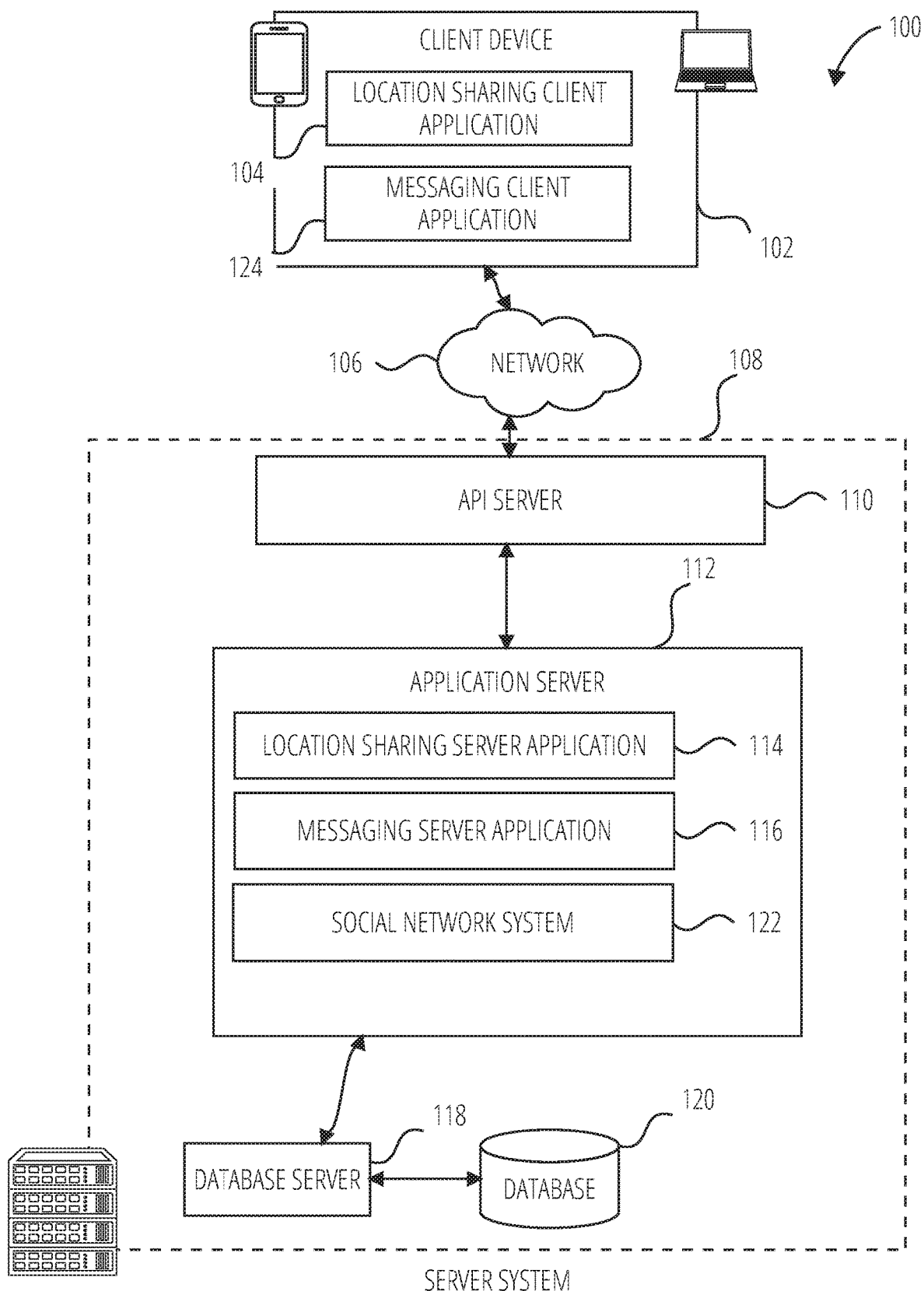
FIG. 1 is a diagrammatic representation of a networked environment in which the present disclosure may be deployed, in accordance with some example embodiments.

Embodiments of the present disclosure provide a geographically-based graphical user interface (GUI). This user interface may be referred to herein as a "map GUI," and may be used in conjunction with a social media application. In some embodiments, the map GUI may include representations of at least approximate respective positions of a user and a user's friends in a social network graph accessed by the social media application using avatars for each respective user.

Various embodiments of the present disclosure provide systems, methods, techniques, instruction sequences, and computing machine program products for predicting a state of a user (e.g., asleep or awake). Conventional methods for determining a user's sleep state are either grossly inaccurate or require invasive access to the user's data.

Motivated by these challenges, some embodiments of the present disclosure provide improvements over conventional methods for determining a user's sleep state by accurately detecting a sleep state of the user with limited access to the user's data. In some embodiments, some of these improvements are achieved by analyzing the user's historical activity data to extract sleep patterns specific to the user. These sleep patterns are then used to more accurately predict a sleep state of the user.

For example, in some embodiments, the location sharing system accesses historical activity data of the user and extracts historical sleep records from the historical activity data. The system clusters the historical sleep records into a plurality of clusters and extracts a sleep pattern from each one of the plurality of clusters. Then, when the location sharing system receives current activity data of the user, the system can predict whether the user is currently asleep based on the current activity of the user and at least one of the sleep patterns. Some embodiments additionally compute an estimated wake up time of the user.

Some embodiments share the predicted physiological state of the user with the user's approved contact or friend accounts via the map GUI. Some embodiments additionally share the estimated wake up time of the user. In various embodiments, such data sharing is turned off by default, and the data is only shared if selected for sharing by a privacy setting update provided by the user.

The present disclosure provides various improvements over conventional user interfaces. In particular, some embodiments allow a user to immediately access information about the physiological state of other users via a map GUI. This can help a user interact with users who are awake and refrain from interacting with users who are asleep.

The description that follows includes systems, methods, techniques, instruction sequences, and computing machine program products that embody illustrative embodiments of the disclosure. In the following description, for the purposes of explanation, numerous specific details are set forth in order to provide an understanding of various embodiments of the inventive subject matter. It will be evident, however, to those skilled in the art, that embodiments of the inventive subject matter may be practiced without these specific details. In general, well-known instruction instances, protocols, structures, and techniques are not necessarily shown in detail.

FIG. 1 is a block diagram showing an example location sharing system 100 for exchanging location data over a network. The location sharing system 100 includes multiple instances of a client device 102, each of which hosts a number of applications including a location sharing client application 104. Each location sharing client application 104 is communicatively coupled to other instances of the location sharing client application 104 and a location sharing server system 108 via a network 106 (e.g., the Internet).

A location sharing client application 104 is able to communicate and exchange data with another location sharing client application 104 and with the location sharing server system 108 via the network 106. The data exchanged between location sharing client application 104, and between a location sharing client application 104 and the location sharing server system 108, includes functions (e.g., commands to invoke functions) as well as payload data (e.g., location data, text, audio, video or other multimedia data).

The location sharing server system 108 provides server-side functionality via the network 106 to a particular location sharing client application 104. While certain functions of the location sharing system 100 are described herein as being performed by either a location sharing client application 104 or by the location sharing server system 108, the location of certain functionality either within the location sharing client application 104 or the location sharing server system 108 is a design choice. For example, it may be technically preferable to initially deploy certain technology and functionality within the location sharing server system 108, but to later migrate this technology and functionality to the location sharing client application 104 where a client device 102 has a sufficient processing capacity.

The location sharing server system 108 supports various services and operations that are provided to the location sharing client application 104. Such operations include transmitting data to, receiving data from, and processing data generated by the location sharing client application 104. This data may include geolocation information, message content, client device information, media annotation and overlays, message content persistence conditions, social network information, and live event information, as examples. Data exchanges within the location sharing system 100 are invoked and controlled through functions available via user interfaces (UIs) of the location sharing client application 104.

Turning now specifically to the location sharing server system 108, an Application Program Interface (API) server 110 is coupled to, and provides a programmatic interface to, an application server 112. The application server 112 is communicatively coupled to a database server 118, which facilitates access to a database 120 in which is stored data associated with messages processed by the application server 112.

The API server 110 receives and transmits message data (e.g., commands and message payloads) between the client device 102 and the application server 112. Specifically, the API server 110 provides a set of interfaces (e.g., routines and protocols) that can be called or queried by the location sharing client application 104 in order to invoke functionality of the application server 112. The API server 110 exposes various functions supported by the application server 112, including account registration, login functionality, the sending of messages, via the application server 112, from a particular location sharing client application 104 to another location sharing client application 104; the sending of media files (e.g., images or video) from a location sharing client application 104 to the location sharing server application 114 and for possible access by another location sharing client application 104; the setting of a collection of media data (e.g., story); the retrieval of a list of friends of a user of a client device 102; the retrieval of such collections; the retrieval of messages and content; the adding and deletion of friends to a social graph; the location of friends within a social graph; and opening an application event (e.g., relating to the location sharing client application 104).

The application server 112 hosts a number of applications and subsystems, including a location sharing server application 114, a messaging server application 116 (part of a messaging system 200), and a social network system 122.

Examples of functions and services supported by the location sharing server application 114 include generating a map GUI. In some embodiments, the map GUI may include representations of at least approximate respective positions of a user and a user's friends in a social network graph accessed by the social media application using avatars for each respective user.

The location sharing server application 114 may receive user authorization to use, or refrain from using, the user's location information. In some embodiments, the location sharing server application 114 may likewise opt to share or not share the user's location with others via the map GUI. In some cases, the user's avatar may be displayed to the user on the display screen of the user's computing device regardless of whether the user is sharing his or her location with other users.

In some embodiments, a user can select groups of other users (audiences) to which his/her location will be displayed and may specify different display attributes for the different respective groups or for different respective individuals. In one example, audience options include: "Best Friends," "Friends," and "Custom" (which is an individual-level whitelist of people). In this example, if "Friends" is selected, all new people added to the user's friends list will automatically be able to see their location. If they are already sharing with the user, their avatars will appear on the user's map.

In some embodiments, when viewing the map GUI, the user is able to see the location of all his/her friends that have shared their location with the user on the map, with each friend represented by their respective avatar. In some embodiments, if a friend does not have an avatar, the friend may be represented using a profile picture or a default icon displayed at the corresponding location for the friend.

In some embodiments, the user can select between friends on the map via a menu, such as a carousel. In some embodiments, selecting a particular friend automatically centers the map view on the avatar of that friend. Embodiments of the present disclosure may also allow the user to take a variety of actions with the user's friends from within the map GUI. For example, the system may allow the user to chat with the user's friends without leaving the map. In one particular example, the user may select a chat icon from a menu presented in conjunction with the map GUI to initiate a chat session.

The client device 102 host a messaging client application 124 (part of the messaging system 200). The messaging server application 116 implements a number of message processing technologies and functions, particularly related to the aggregation and other processing of content (e.g., textual and multimedia content) included in messages received from multiple instances of the location sharing client application 104. As will be described in further detail, the text and media content from multiple sources may be aggregated into collections of content (e.g., called stories or galleries). These collections are then made available, by the location sharing server application 114, to the location sharing client application 104. Other processor and memory intensive processing of data may also be performed server-side by the location sharing server application 114, in view of the hardware requirements for such processing.

The application server 112 is communicatively coupled to a database server 118, which facilitates access to a database 120 in which is stored data processed by the location sharing server application 114.

Figure 3:
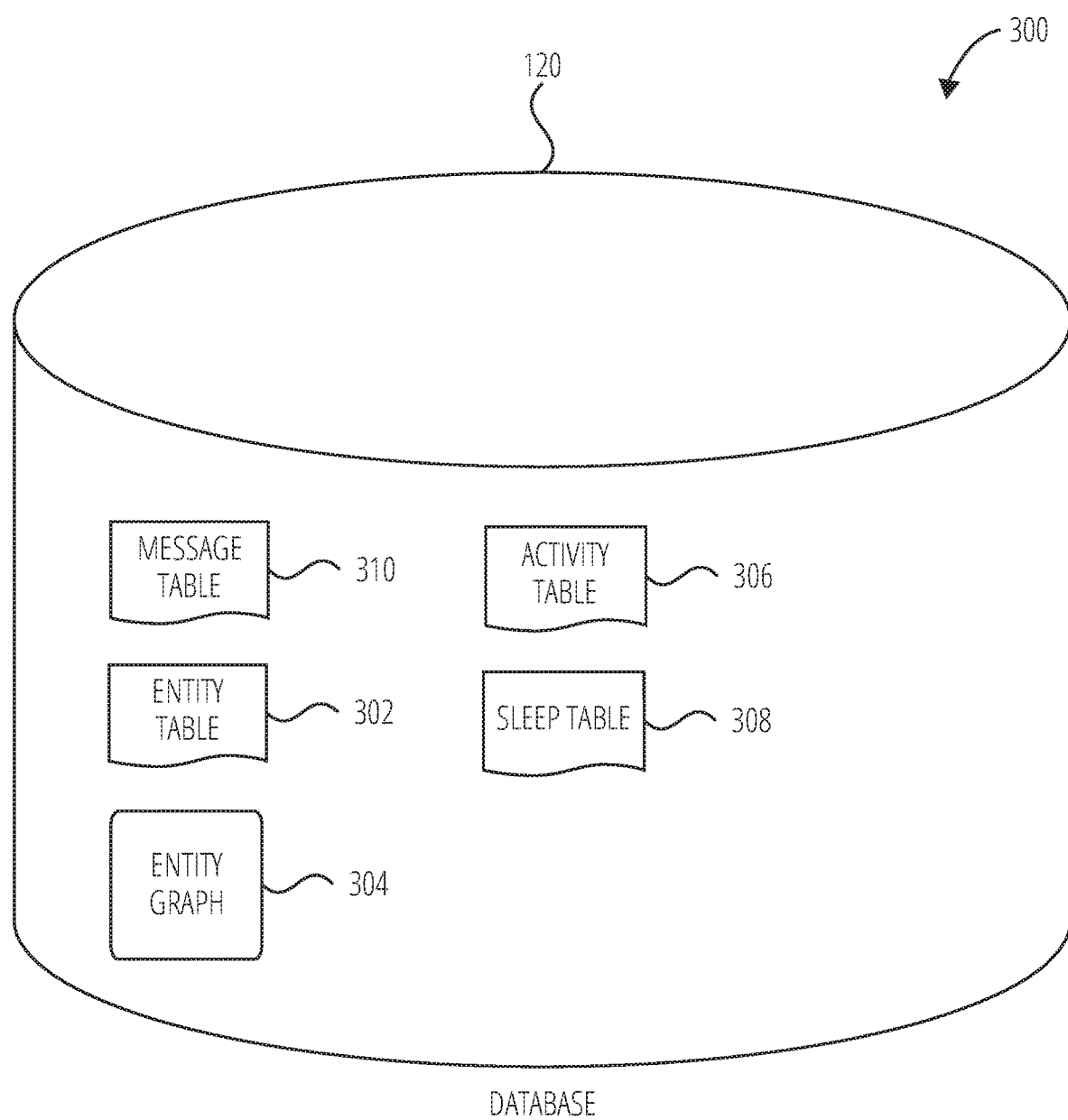
FIG. 3 is a diagrammatic representation of a data structure as maintained in a database, in accordance with some example embodiments.

The social network system 122 supports various social networking functions and services, and makes these functions and services available to the location sharing server application 114. To this end, the social network system 122 maintains and accesses an entity graph 304 (as shown in FIG. 3) within the database 120. Examples of functions and services supported by the social network system 122 include the identification of other users of the location sharing system 100 with which a particular user has relationships or is "following," and also the identification of other entities and interests of a particular user.

Figure 2:
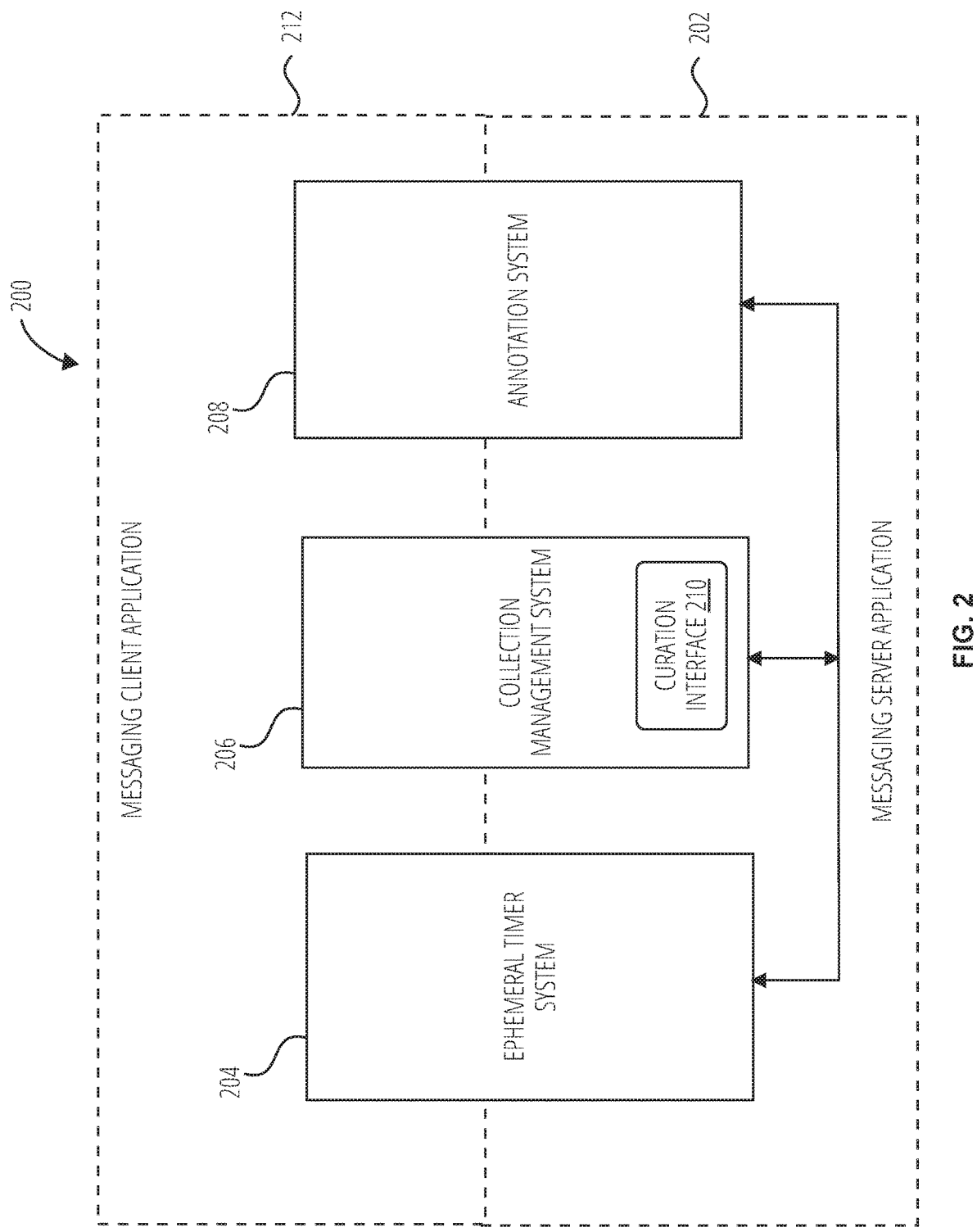
FIG. 2 is a diagrammatic representation of a messaging system, in accordance with some example embodiments.

FIG. 2 is block diagram illustrating further details regarding the messaging system 200, according to example embodiments. Specifically, the messaging system 200 includes the messaging server application 116 and the messaging client application 124, which in turn embody a number of subsystems, namely an ephemeral timer system 202, a collection management system 204, and an annotation system 206.

The ephemeral timer system 202 is responsible for enforcing the temporary access to content permitted by the messaging client application 124 and the location sharing server application 114. To this end, the ephemeral timer system 202 incorporates a number of timers that, based on duration and display parameters associated with a message, or collection of messages (e.g., a story), selectively display and enable access to messages and associated content via the messaging client application 124. Further details regarding the operation of the ephemeral timer system 202 are provided below.

The collection management system 204 is responsible for managing collections of media (e.g., collections of text, image video and audio data). In some examples, a collection of content (e.g., messages, including images, video, text and audio) may be organized into an "event gallery" or an "event story." Such a collection may be made available for a specified time period, such as the duration of an event to which the content relates. For example, content relating to a music concert may be made available as a "story" for the duration of that music concert. The collection management system 204 may also be responsible for publishing an icon that provides notification of the existence of a particular collection to the user interface of the messaging client application 124.

The collection management system 204 furthermore includes a curation interface 208 that allows a collection manager to manage and curate a particular collection of content. For example, the curation interface 208 enables an event organizer to curate a collection of content relating to a specific event (e.g., delete inappropriate content or redundant messages). Additionally, the collection management system 204 employs machine vision (or image recognition technology) and content rules to automatically curate a content collection. In certain embodiments, compensation may be paid to a user for inclusion of user-generated content into a collection. In such cases, the curation interface 208 operates to automatically make payments to such users for the use of their content.

The annotation system 206 provides various functions that enable a user to annotate or otherwise modify or edit media content associated with a message. For example, the annotation system 206 provides functions related to the generation and publishing of media overlays for messages processed by the location sharing system 100. The annotation system 206 operatively supplies a media overlay or supplementation (e.g., an image filter) to the messaging client application 124 based on a geolocation of the client device 102. In another example, the annotation system 206 operatively supplies a media overlay to the messaging client application 124 based on other information, such as social network information of the user of the client device 102. A media overlay may include audio and visual content and visual effects. Examples of audio and visual content include pictures, texts, logos, animations, and sound effects. An example of a visual effect includes color overlaying. The audio and visual content or the visual effects can be applied to a media content item (e.g., a photo) at the client device 102. For example, the media overlay may include text that can be overlaid on top of a photograph taken by the client device 102. In another example, the media overlay includes an identification of a location overlay (e.g., Venice beach), a name of a live event, or a name of a merchant overlay (e.g., Beach Coffee House). In another example, the annotation system 206 uses the geolocation of the client device 102 to identify a media overlay that includes the name of a merchant at the geolocation of the client device 102. The media overlay may include other indicia associated with the merchant. The media overlays may be stored in the database 120 and accessed through the database server 118.

In one example embodiment, the annotation system 206 provides a user-based publication platform that enables users to select a geolocation on a map and upload content associated with the selected geolocation. The user may also specify circumstances under which a particular media overlay should be offered to other users. The annotation system 206 generates a media overlay that includes the uploaded content and associates the uploaded content with the selected geolocation.

In another example embodiment, the annotation system 206 provides a merchant-based publication platform that enables merchants to select a particular media overlay associated with a geolocation via a bidding process. For example, the annotation system 206 associates the media overlay of a highest bidding merchant with a corresponding geolocation for a predefined amount of time.

FIG. 3 is a schematic diagram illustrating data structures 300, which may be stored in the database 120 of the location sharing server system 108, according to certain example embodiments. While the content of the database 120 is shown to comprise a number of tables, it will be appreciated that the data could be stored in other types of data structures (e.g., as an object-oriented database).

The database 120 includes message data stored within a message table 310. An entity table 302 stores entity data, including an entity graph 304. Entities for which records are maintained within the entity table 302 may include individuals (e.g., users), corporate entities, organizations, objects, places, events, and so forth. Regardless of type, any entity regarding which the location sharing server system 108 stores data may be a recognized entity. Each entity is provided with a unique identifier, as well as an entity type identifier (not shown). The entity graph 304 furthermore stores information regarding relationships and associations between entities. Such relationships may be social, professional (e.g., work at a common corporation or organization), interested-based, or activity-based, merely for example. An activity table 306 stores historical and current activity data of users (e.g., geolocation information of client devices (e.g., client device 102) determined by a satellite-based radio navigation system such as the Global Positioning System (GPS), and user interactions with the user's client devices (e.g., client device 102)). A sleep table 308 stores historical and current sleep data of users (e.g., sleep records and sleep patterns).

Figure 4:
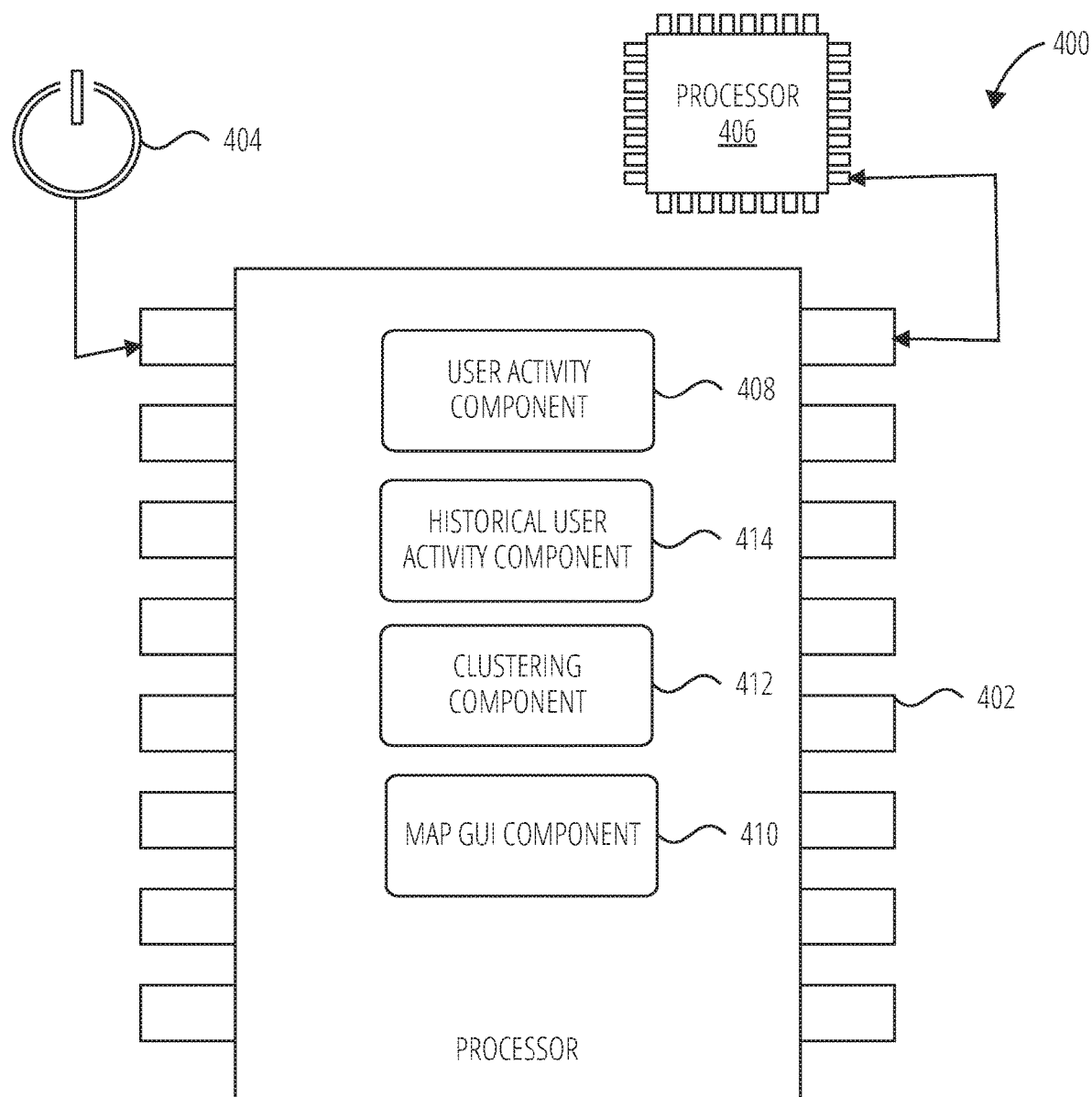
FIG. 4 is a diagrammatic representation of a processing environment, in accordance with some example embodiments.

Turning now to FIG. 4, there is shown a diagrammatic representation of a processing environment 400, which includes at least a processor 402 (e.g., a GPU, CPU or combination thereof).

The processor 402 is shown to be coupled to a power source 404, and to include (either permanently configured or temporarily instantiated) modules, namely a user activity component 408, a historical user activity component 414, a clustering component 412, and a map GUI component 410. The user activity component 408 operationally predicts a state of a user based on activity data of the user. The historical user activity component 408 generates historical activity data of a user by consolidating activity data collected over time from one or more client devices (e.g., client device 102) associated with the user. The clustering component 412 accesses historical user activity data of a user and generates sleep pattern(s) of the user. The map GUI component 410 operationally generates user interfaces and causes the user interfaces to be displayed on client devices. As illustrated, the processor 402 may be communicatively coupled to another processor 406.

Figure 5:
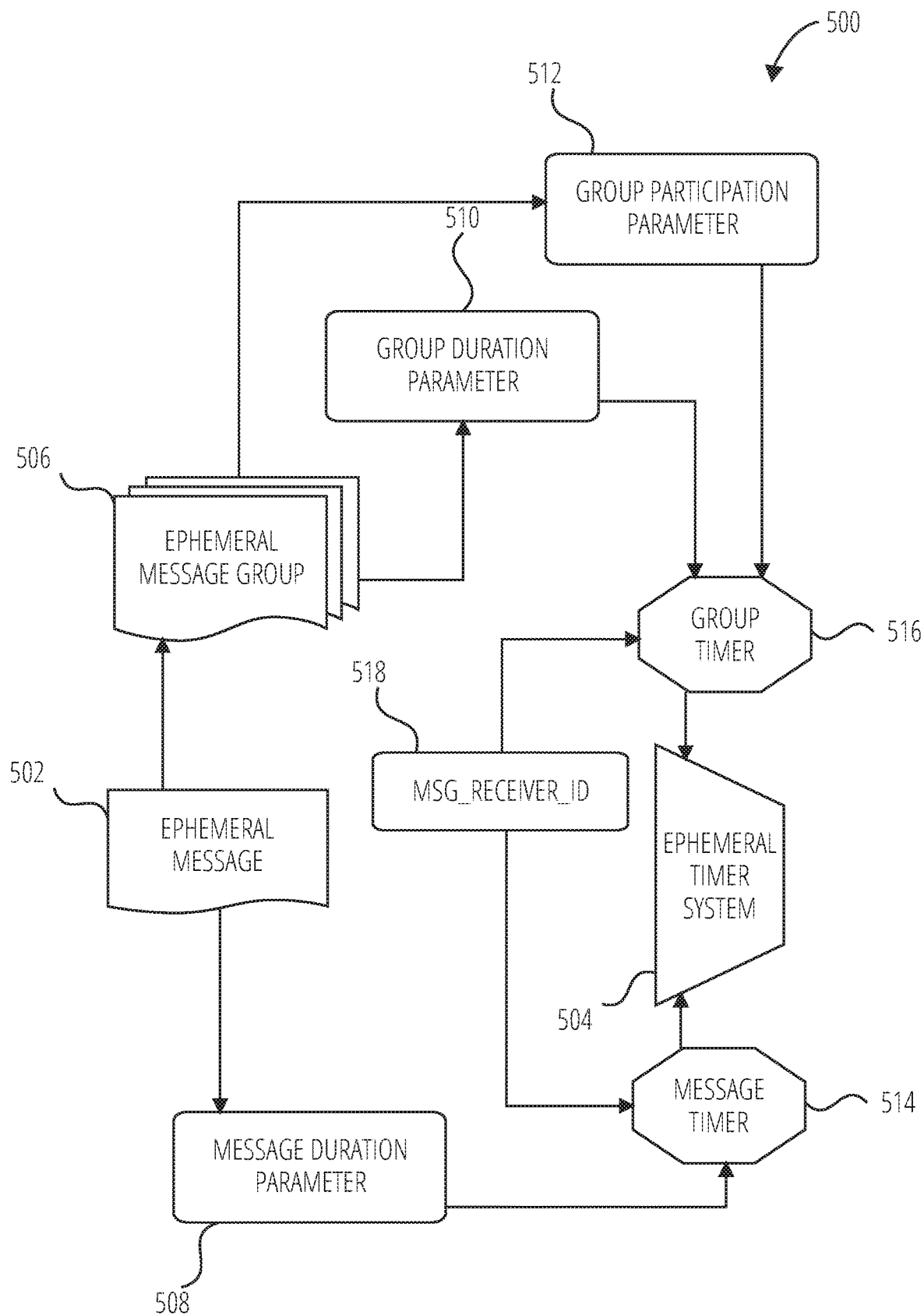
FIG. 5 is a flowchart for an access-limiting process, in accordance with some example embodiments.

FIG. 5 is a schematic diagram illustrating an access-limiting process 500, in terms of which access to content (e.g., an ephemeral message 502, and associated multimedia payload of data) or a content collection (e.g., an ephemeral message group 506) may be time-limited (e.g., made ephemeral).

An ephemeral message 502 is shown to be associated with a message duration parameter 508, the value of which determines an amount of time that the ephemeral message 502 will be displayed to a receiving user of the ephemeral message 502 by the location sharing client application 104. In one embodiment, an ephemeral message 502 is viewable by a receiving user for up to a maximum of 10 seconds, depending on the amount of time that the sending user specifies using the message duration parameter 508.

The message duration parameter 508 and a message receiver identifier 518 are shown to be inputs to a message timer 514, which is responsible for determining the amount of time that the ephemeral message 502 is shown to a particular receiving user identified by the message receiver identifier 518. In particular, the ephemeral message 502 will only be shown to the relevant receiving user for a time period determined by the value of the message duration parameter 508. The message timer 514 is shown to provide output to a more generalized ephemeral timer system 504, which is responsible for the overall timing of display of content (e.g., an ephemeral message 502) to a receiving user.

The ephemeral message 502 is shown in FIG. 5 to be included within an ephemeral message group 506 (e.g., a collection of messages in a personal story, or an event story). The ephemeral message group 506 has an associated group duration parameter 510, a value of which determines a time-duration for which the ephemeral message group 506 is presented and accessible to users of the location sharing system 100. The group duration parameter 510, for example, may be the duration of a music concert, where the ephemeral message group 506 is a collection of content pertaining to that concert. Alternatively, a user (either the owning user or a curator user) may specify the value for the group duration parameter 510 when performing the setup and creation of the ephemeral message group 506.

Additionally, each ephemeral message 502 within the ephemeral message group 506 has an associated group participation parameter 512, a value of which determines the duration of time for which the ephemeral message 502 will be accessible within the context of the ephemeral message group 506. Accordingly, a particular ephemeral message group 506 may "expire" and become inaccessible within the context of the ephemeral message group 506, prior to the ephemeral message group 506 itself expiring in terms of the group duration parameter 510. The group duration parameter 510, group participation parameter 512, and message receiver identifier 518 each provide input to a group timer 516, which operationally determines, firstly, whether a particular ephemeral message 502 of the ephemeral message group 506 will be displayed to a particular receiving user and, if so, for how long. Note that the ephemeral message group 506 is also aware of the identity of the particular receiving user as a result of the message receiver identifier 518.

Accordingly, the group timer 516 operationally controls the overall lifespan of an associated ephemeral message group 506, as well as an individual ephemeral message 502 included in the ephemeral message group 506. In one embodiment, each and every ephemeral message 502 within the ephemeral message group 506 remains viewable and accessible for a time-period specified by the group duration parameter 510. In a further embodiment, a certain ephemeral message 502 may expire, within the context of ephemeral message group 506, based on a group participation parameter 512. Note that a message duration parameter 508 may still determine the duration of time for which a particular ephemeral message 502 is displayed to a receiving user, even within the context of the ephemeral message group 506. Accordingly, the message duration parameter 508 determines the duration of time that a particular ephemeral message 502 is displayed to a receiving user, regardless of whether the receiving user is viewing that ephemeral message 502 inside or outside the context of an ephemeral message group 506.

The ephemeral timer system 504 may furthermore operationally remove a particular ephemeral message 502 from the ephemeral message group 506 based on a determination that it has exceeded an associated group participation parameter 512. For example, when a sending user has established a group participation parameter 512 of 24 hours from posting, the ephemeral timer system 504 will remove the relevant ephemeral message 502 from the ephemeral message group 506 after the specified 24 hours. The ephemeral timer system 504 also operates to remove an ephemeral message group 506 either when the group participation parameter 512 for each and every ephemeral message 502 within the ephemeral message group 506 has expired, or when the ephemeral message group 506 itself has expired in terms of the group duration parameter 510.

In certain use cases, a creator of a particular ephemeral message group 506 may specify an indefinite group duration parameter 510. In this case, the expiration of the group participation parameter 512 for the last remaining ephemeral message 502 within the ephemeral message group 506 will determine when the ephemeral message group 506 itself expires. In this case, a new ephemeral message 502, added to the ephemeral message group 506, with a new group participation parameter 512, effectively extends the life of an ephemeral message group 506 to equal the value of the group participation parameter 512.

Responsive to the ephemeral timer system 504 determining that an ephemeral message group 506 has expired (e.g., is no longer accessible), the ephemeral timer system 504 communicates with the location sharing system 100 (and, for example, specifically the location sharing client application 104) to cause an indicium (e.g., an icon) associated with the relevant ephemeral message group 506 to no longer be displayed within a user interface of the location sharing client application 104. Similarly, when the ephemeral timer system 202 determines that the message duration parameter 508 for a particular ephemeral message 502 has expired, the ephemeral timer system 504 causes the location sharing client application 104 to no longer display an indicium (e.g., an icon or textual identification) associated with the ephemeral message 502.

Figure 6:
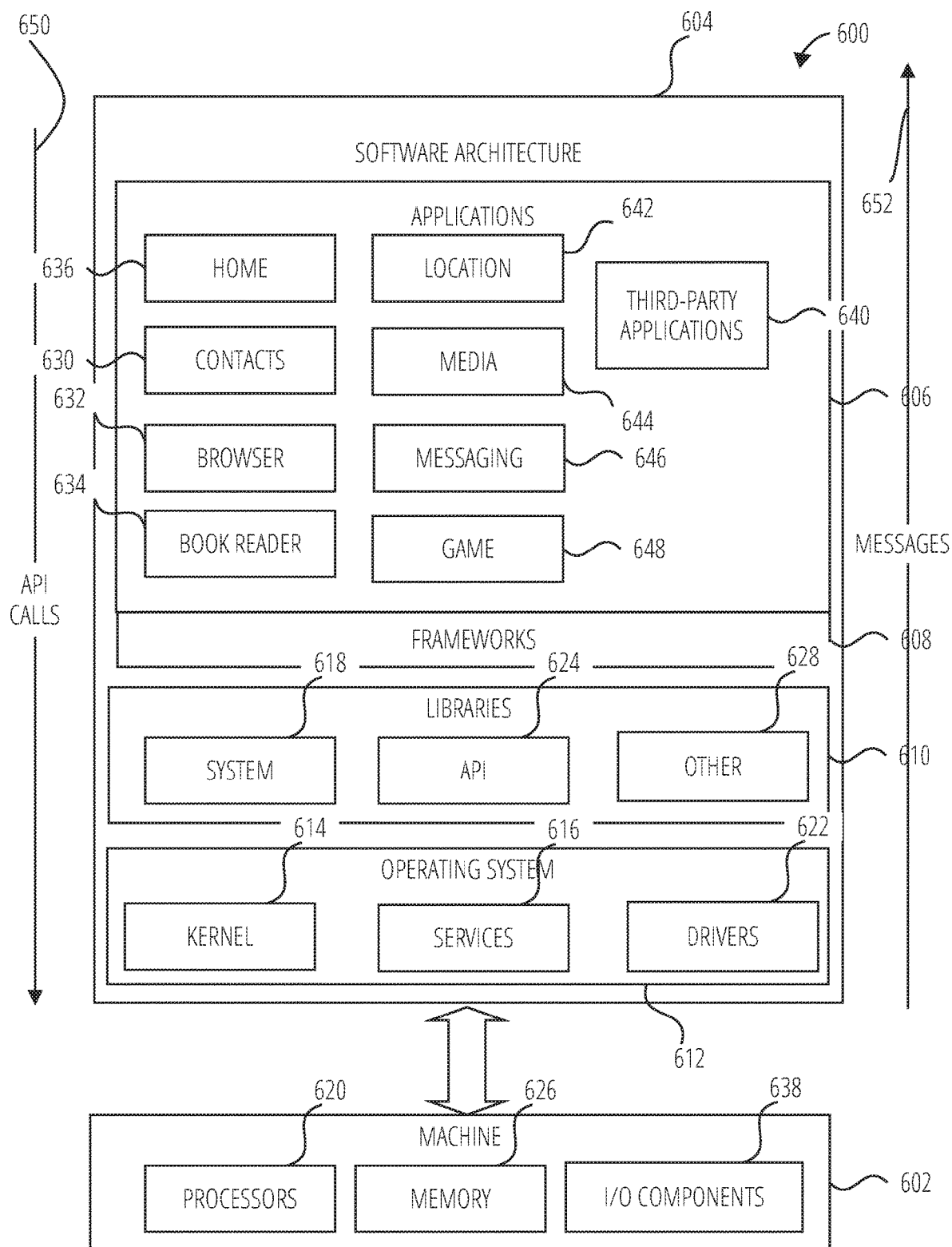
FIG. 6 is block diagram showing a software architecture within which the present disclosure may be implemented, in accordance with some example embodiments.

FIG. 6 is a block diagram 600 illustrating a software architecture 604, which can be installed on any one or more of the devices described herein. The software architecture 604 is supported by hardware such as a machine 602 that includes processors 620, memory 626, and input/output (I/O) components 638. In this example, the software architecture 604 can be conceptualized as a stack of layers, where each layer provides a particular functionality. The software architecture 604 includes layers such as an operating system 612, libraries 610, frameworks 608, and applications 606. Operationally, the applications 606 invoke API calls 650 through the software stack and receive messages 652 in response to the API calls 650.

The operating system 612 manages hardware resources and provides common services. The operating system 612 includes, for example, a kernel 614, services 616, and drivers 622. The kernel 614 acts as an abstraction layer between the hardware and the other software layers. For example, the kernel 614 provides memory management, processor management (e.g., scheduling), component management, networking, and security settings, among other functionality. The services 616 can provide other common services for the other software layers. The drivers 622 are responsible for controlling or interfacing with the underlying hardware. For instance, the drivers 622 can include display drivers, camera drivers, BLUETOOTH® or BLUETOOTH® Low Energy drivers, flash memory drivers, serial communication drivers (e.g., Universal Serial Bus (USB) drivers), WI-FI® drivers, audio drivers, power management drivers, and so forth.

The libraries 610 provide a low-level common infrastructure used by the applications 606. The libraries 610 can include system libraries 618 (e.g., C standard library) that provide functions such as memory allocation functions, string manipulation functions, mathematic functions, and the like. In addition, the libraries 610 can include API libraries 624 such as media libraries (e.g., libraries to support presentation and manipulation of various media formats such as Moving Picture Experts Group-4 (MPEG4). Advanced Video Coding (H.264 or AVC). Moving Picture Experts Group Layer-3 (MP3), Advanced Audio Coding (AAC), Adaptive Multi-Rate (AMR) audio codec. Joint Photographic Experts Group (JPEG or JPG), or Portable Network Graphics (PNG)), graphics libraries (e.g., an OpenGL framework used to render in two dimensions (2D) and three dimensions (3D) in a graphic content on a display), database libraries (e.g., SQLite to provide various relational database functions), web libraries (e.g., WebKit to provide web browsing functionality), and the like. The libraries 610 can also include a wide variety of other libraries 628 to provide many other APIs to the applications 606.

The frameworks 608 provide a high-level common infrastructure that is used by the applications 606. For example, the frameworks 608 provide various GUI functions, high-level resource management, and high-level location services. The frameworks 608 can provide a broad spectrum of other APIs that can be used by the applications 606, some of which may be specific to a particular operating system or platform.

In an example embodiment, the applications 606 may include a home application 636, a contacts application 630, a browser application 632, a book reader application 634, a location application 642, a media application 644, a messaging application 646, a game application 648, and a broad assortment of other applications such as third-party applications 640. The applications 606 are programs that execute functions defined in the programs. Various programming languages can be employed to create one or more of the applications 606, structured in a variety of manners, such as object-oriented programming languages (e.g., Objective-C, Java, or C++) or procedural programming languages (e.g., C or assembly language). In a specific example, the third-party applications 640 (e.g., applications developed using the ANDROID™ or IOS™ software development kit (SDK) by an entity other than the vendor of the particular platform) may be mobile software running on a mobile operating system such as IOS™. ANDROID™, WINDOWS® Phone, or another mobile operating system. In this example, the third-party applications 640 can invoke the API calls 650 provided by the operating system 612 to facilitate functionality described herein.

Figure 7:
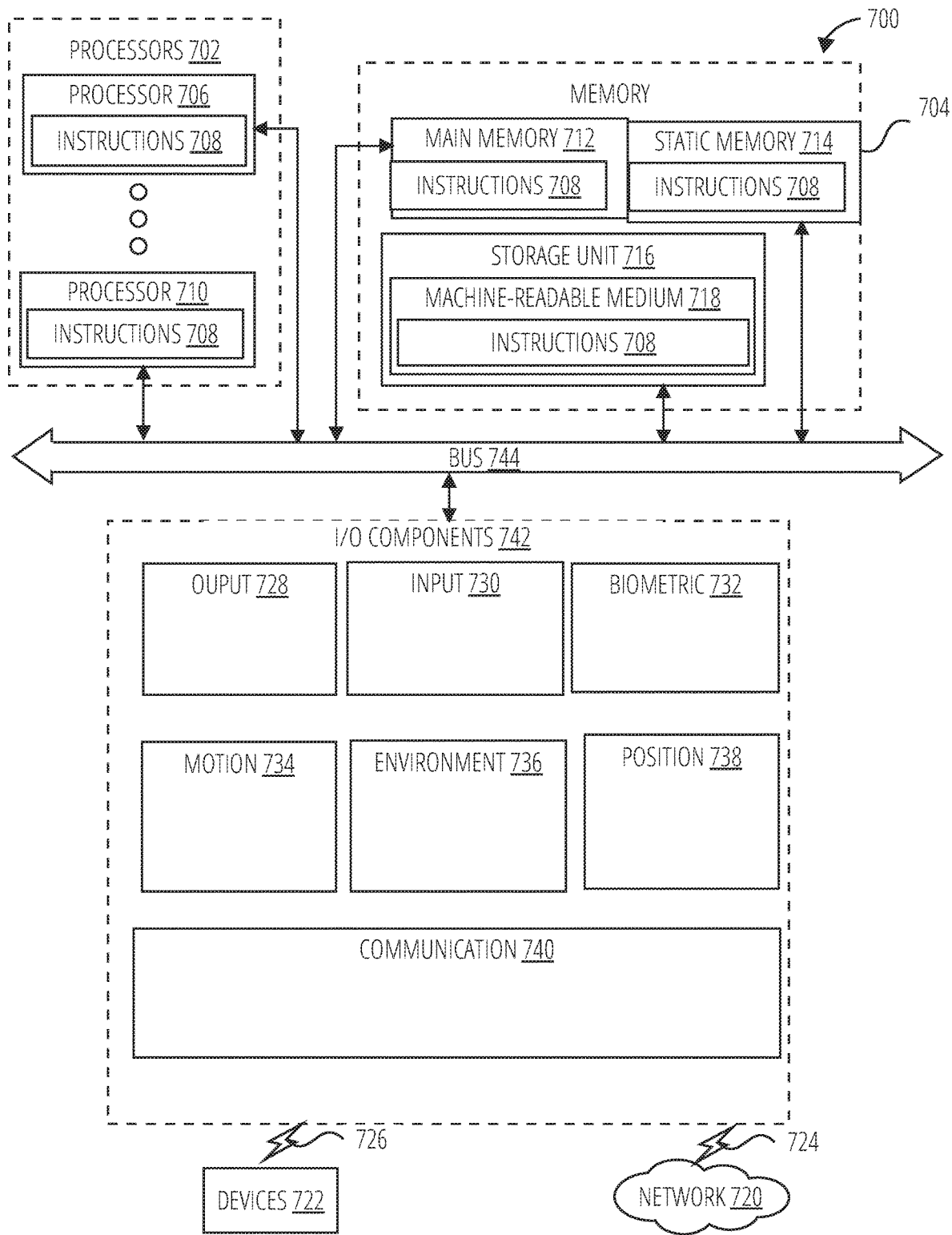
FIG. 7 is a diagrammatic representation of a machine, in the form of a computer system within which a set of instructions may be executed for causing the machine to perform any one or more of the methodologies discussed, in accordance with some example embodiments.

FIG. 7 is a diagrammatic representation of a machine 700 within which instructions 708 (e.g., software, a program, an application, an applet, an app, or other executable code) for causing the machine 700 to perform any one or more of the methodologies discussed herein may be executed. For example, the instructions 708 may cause the machine 700 to execute any one or more of the methods described herein. The instructions 708 transform the general, non-programmed machine 700 into a particular machine 700 programmed to carry out the described and illustrated functions in the manner described. The machine 700 may operate as a standalone device or may be coupled (e.g., networked) to other machines. In a networked deployment, the machine 700 may operate in the capacity of a server machine or a client machine in a server-client network environment, or as a peer machine in a peer-to-peer (or distributed) network environment. The machine 700 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 708, sequentially or otherwise, that specify actions to be taken by the machine 700. Further, while only a single machine 700 is illustrated, the term "machine" shall also be taken to include a collection of machines that individually or jointly execute the instructions 708 to perform any one or more of the methodologies discussed herein.

The machine 700 may include processors 702, memory 704, and I/O components 742, which may be configured to communicate with each other via a bus 744. In an example embodiment, the processors 702 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an ASIC, a Radio-Frequency Integrated Circuit (RFIC), another processor, or any suitable combination thereof) may include, for example, a processor 706 and a processor 710 that execute the instructions 708. The term "processor" is intended to include multi-core processors that may comprise two or more independent processors (sometimes referred to as "cores") that may execute instructions contemporaneously. Although FIG. 7 shows multiple processors 702, the machine 700 may include a single processor with a single core, a single processor with multiple cores (e.g., a multi-core processor), multiple processors with a single core, multiple processors with multiples cores, or any combination thereof.

The memory 704 includes a main memory 712, a static memory 714, and a storage unit 716, both accessible to the processors 702 via the bus 744. The main memory 704, the static memory 714, and storage unit 716 store the instructions 708 embodying any one or more of the methodologies or functions described herein. The instructions 708 may also reside, completely or partially, within the main memory 712, within the static memory 714, within machine-readable medium 718 within the storage unit 716, within at least one of the processors 702 (e.g., within the processor's cache memory), or any suitable combination thereof, during execution thereof by the machine 700.

The I/O components 742 may include a wide variety of components to receive input, provide output, produce output, transmit information, exchange information, capture measurements, and so on. The specific I/O components 742 that are included in a particular machine will depend on the type of machine. For example, portable machines such as mobile phones may include a touch input device or other such input mechanisms, while a headless server machine will likely not include such a touch input device. It will be appreciated that the I/O components 742 may include many other components that are not shown in FIG. 7. In various example embodiments, the I/O components 742 may include output components 728 and input components 730. The output components 728 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 730 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or another pointing instrument), tactile input components (e.g., a physical button, a touch screen that provides location and/or force of touches or touch gestures, or other tactile input components), audio input components (e.g., a microphone), and the like.

In further example embodiments, the I/O components 742 may include biometric components 732, motion components 734, environmental components 736, or position components 738, among a wide array of other components. For example, the biometric components 732 include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram-based identification), and the like. The motion components 734 include acceleration sensor components (e.g., accelerometer), gravitation sensor components, rotation sensor components (e.g., gyroscope), and so forth. The environmental components 736 include, for example, illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 738 include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 742 further include communication components 740 operable to couple the machine 700 to a network 720 or devices 722 via a coupling 724 and a coupling 726, respectively. For example, the communication components 740 may include a network interface component or another suitable device to interface with the network 720. In further examples, the communication components 740 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 722 may be another machine or any of a wide variety of peripheral devices (e.g., a peripheral device coupled via a USB).

Moreover, the communication components 740 may detect identifiers or include components operable to detect identifiers. For example, the communication components 740 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code. Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 740, such as location via Internet Protocol (IP) geolocation, location via Wi-Fi® signal triangulation, location via detecting an NFC beacon signal that may indicate a particular location, and so forth.

The various memories (e.g., memory 704, main memory 712, static memory 714, and/or memory of the processors 702) and/or storage unit 716 may store one or more sets of instructions and data structures (e.g., software) embodying or used by any one or more of the methodologies or functions described herein. These instructions (e.g., the instructions 708), when executed by processors 702, cause various operations to implement the disclosed embodiments.

The instructions 708 may be transmitted or received over the network 720, using a transmission medium, via a network interface device (e.g., a network interface component included in the communication components 740) and using any one of a number of well-known transfer protocols (e.g., hypertext transfer protocol (HTTP)). Similarly, the instructions 708 may be transmitted or received using a transmission medium via the coupling 726 (e.g., a peer-to-peer coupling) to the devices 722.

Figure 8:
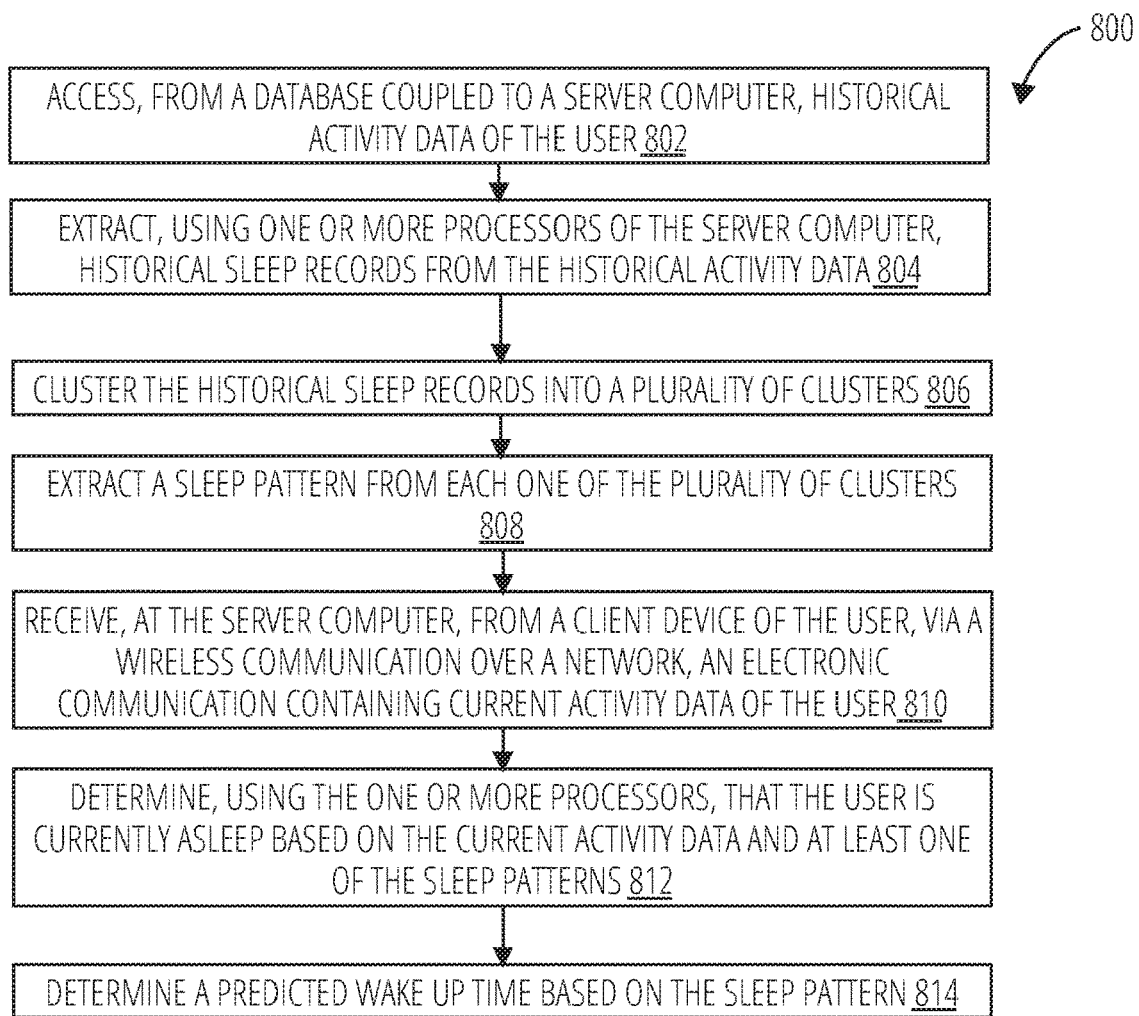
FIG. 8 illustrates a method, in accordance with one embodiment.

FIG. 8 is a flowchart illustrating a method 800 for identifying a physiological state of a user (e.g., asleep, awake). The method 800 may be embodied in computer-readable instructions for execution by one or more processors (e.g., processor 402) such that the steps of the method 800 may be performed in part or in whole by functional components (e.g., user activity component 408, historical user activity component 414, clustering component 412, map GUI component 410) of a processing environment 400 of a system (e.g., application server 112); accordingly, the method 800 is described below by way of example with reference thereto. However, it shall be appreciated that the method 800 may be deployed on various other hardware configurations and is not intended to be limited to the functional components of the processing environment 400.

In block 802, the system accesses, from a database (e.g., database 120) coupled to a server computer (e.g., application server 112), the user's historical activity data. The user's historical activity data may be generated by consolidating instant activity data collected over time from one or more client devices (e.g., client device 102) associated with the user. The activity data may include location data. The location data may include a plurality of points, each point being defined by at least a set of geographical coordinates and a time stamp. The location data may be generated by one or more location sensors (e.g., position components 738) coupled to the client device. In some embodiments, the location sensors may include a GPS component integrated in the client device, as well as other types of location sensors. The activity data may further include user interaction data. User interaction data may include user interactions with a client device or with a specific application running on a client device. A user interaction may be any sort of user input detected by a client device of the user, via any sort of user interface, such as a touch user interface or a voice user interface. The activity data may further include any other type of user data indicative of the activity of the user.

The system may need to receive authorization from the user to utilize activity data from the user's client devices prior to performing the remaining steps of method 800. Such authorization may be obtained via acceptance of a terms of service for utilizing an online social network or other service provided by the system, by acceptance on a case-by-case basis by the first user (e.g., via popups displayed on the user's computing device) or using any other suitable method for obtaining authorization by the user(s).

In block 804, the system extracts historical sleep records from the user's historical activity data. A sleep record is a timetable indicating probability of the user being asleep (e.g., asleep or awake) for a plurality of historical time slots (e.g., Monday 8 am-8:15 am, Jan. 7, 2019; Monday 8 am-8:15 am. Jan. 14, 2019; Monday 8 am-8:15 am, Jan. 21, 2019). For each historical time slot, a probability of the user being asleep during said historical time slot is computed based on the historical activity data having a timestamp included in said historical time slot. In particular, the probability of the user being asleep during said historical time slot may be computed based on the historical activity during said historical time slot verifying a set of criteria.

The set of criteria may include one or more of the following criteria suggesting that the user is asleep:
  a client device of the user is static (e.g., no movement of the client device has been detected for a certain period);
  no user input detected by a client device of the user (e.g., no user input has been detected by the client device for a certain period);
  the user is not surrounded by friends (e.g., a location of the user is not within a preset distance of a location of any of the user's friends);
  the user is at home or at another place where the user is likely to be asleep (e.g., a location of the user is within a geographical scope of the home of the user);
  a client device of the user was recently set on silent mode.

The set of criteria may include one or more of the following criteria suggesting that the user is not asleep:
  a sudden change of the battery charging state of a client device of the user;
  the user moved to another floor (e.g., a sudden change in atmospheric pressure measured by a pressure sensor of a client device of the user);
  the silent mode of a client device of the user was disabled;
  a user input is detected on a client device of the user (e.g., playing a media content like music);
  the user is on the phone (e.g., a client device of the user is in an active telecommunication session);
  the user recently sent a message via the messaging system;
  detection of a movement of a client device of the user (e.g., detection of a non-zero acceleration of the client device detected by an accelerometer embedded in the client device, change in the three dimensional (3D) orientation of the client device in Earth's magnetic field).

At block 806, the system clusters the plurality of sleep records into a plurality of clusters. The plurality of sleep records may be aggregated based on a similarity criterion. For example, the sleep records associated with a category of day (e.g., weekday, weekend day), or a specific day of the week (e.g., Monday) or of the year (e.g., January 1) may be aggregated into a sleep pattern for the specific type of day (e.g., weekday, weekend day), specific day of the week or of the year.

At block 808, a sleep pattern is extracted from each one of the clusters. A sleep pattern is a timetable indicating a probability of a user being asleep for a plurality of generic time slots (e.g., Monday 8 am-8:15 am). For each generic time slot, the probability of a user being asleep is computed by retrieving, from the sleep records included in the cluster, the probabilities computed for historical time slots matching the generic time slot. According to an example, in the Monday sleep pattern, the probability of a user being asleep on Monday 8 am-8:15 am is computed based on the probability of the user being asleep during historical time slots corresponding to Mondays 8 am-8:15 am (e.g., Monday 8 am-8:15 am. Jan. 7, 2019; Monday 8 am-8:15 am, Jan. 14, 2019; Monday 8 am-8:15 am, Jan. 21, 2019). According to another example, in the weekday sleep pattern, the probability of the user being asleep during generic time slot 8 am-8:15 am is computed based on the probability of the user being asleep during historical time slots corresponding to weekdays 8 am-8:15 am (e.g., Monday 8 am-8:15 am. Jan. 7, 2019; Tuesday 8 am-8:15 am, Jan. 8, 2019; Wednesday 8 am-8:15 am, Jan. 9, 2019; Thursday 8 am-8:15 am, Jan. 10, 2019; Friday 8 am-8:15 am, Jan. 11, 2019). In particular, for each generic time slot, the probability of a user being asleep may be computed as an average of the probabilities of the historical time slots matching said generic time slot.

At block 810, the system receives, from a client device (e.g., client device 102) associated with a first user, via a wireless communication, over a network (e.g., network 106), an electronic communication containing current activity data of the first user. As discussed above, the activity data may include location data and user interaction data. The current activity data of the first user may include activity data gathered by one or more of the client devices of the user over a recent period of time. The system may receive activity data on a periodic basis or on an irregular basis and may request data from the client device or receive such data from the client device without such a request. In some embodiments, the client device contains software that monitors the activity data from the client device and transmits updates to the system in response to detecting new activity data. For example, the client device may update the system with a new location only after the location changes by at least a predetermined distance to allow a user to move about a building or other location without triggering updates. Similarly, the client device may update the system with a new user interaction report only when a new user input has been detected.

At block 812, the system determines whether the user is currently asleep based, at least partially, on the current activity data and, at least partially, on at least one of the sleep patterns. For example, a current sleep state of the user may be determined, at least partially, based on the current activity data verifying a set of criteria. The set of criteria may include one or more of the criteria discussed in relation to block 804. In addition, the current sleep state of the user may be determined by selecting at least one sleep pattern corresponding to a current time and retrieving from the selected sleep pattern the probability of the user being asleep at the current time. According to an example, the probability of a user being asleep on Monday 8:05. Jan. 28, 2019 is computed based on the 8 am-8:15 am generic time slot of the Monday sleep pattern. According to another example, the probability of a user being asleep on Monday 8:05, Jan. 28, 2019 is computed based on the 8 am-8:15 am generic time slot of the weekday sleep pattern. If the probability of the user being asleep at the current time exceeds a threshold, the system determines that the user is asleep.

At block 814, the system may compute a predicted wake up time of the user based on the selected sleep pattern. In particular, the predicted wake up time of the user may be determined based on the next generic time slot of the sleep pattern associated with a probability of the user being asleep being below a preset threshold.

Figure 9:
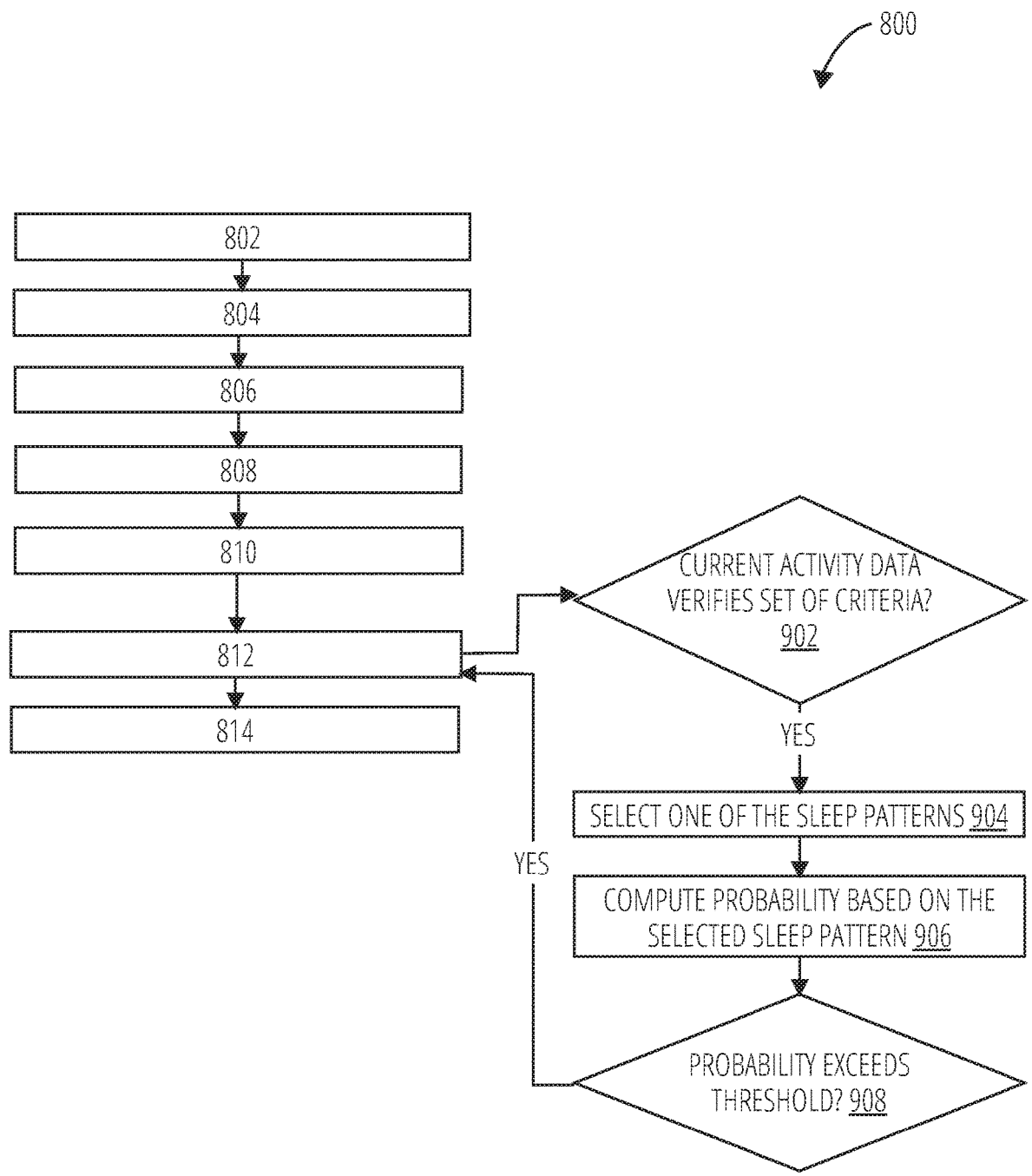
FIG. 9 illustrates a method, in accordance with one embodiment.

As shown in FIG. 9, the method 800 may further include decision block 902, block 904, block 906, and decision block 908, according to some embodiments. Consistent with some embodiments, decision block 902, block 904, block 906, and decision block 908 may be performed as part of (e.g., as sub-blocks or as a subroutine) of block 812, where the system determines that the user is currently asleep.

At decision block 902, the system determines whether the user's current activity data verifies a set of criteria. The set of criteria may include on one or more of the criteria described in relation to block 804.

Based on determining that the user's current activity data does not verify the set of criteria, the user is presumed to be awake.

Based on determining that the user's current activity data verifies the set of criteria, the system selects, at block 904, at least one of the sleep patterns. The at least one sleep pattern may be selected based on the current time. According to an example, if the current day is Monday, Jan. 28, 2019, the system might select the Monday sleep pattern, or the weekday sleep pattern. Additionally or alternatively, the at least one sleep pattern may be selected by correlating the recent user's activity data (e.g., the user's activity data of the last 24 hours) with the each one of the user's sleep patterns and selecting the sleep pattern that correlated best with the recent user's activity data.

At block 906, the system computes a probability of the user being currently asleep based on a current time and the selected sleep pattern. For example, the probability that the user is currently asleep may be computed by retrieving from the sleep pattern the probability of the user being asleep computed for the generic time slot corresponding to the current time. According to an example, the probability of the user being asleep on Monday 8:05 am, Jan. 28, 2019 is computed based on the probability computed for the 8 am-8:15 am generic time slot of the Monday sleep pattern. According to another example, the probability of a user being asleep on Monday 8:05 am, Jan. 28, 2019 is computed based on the probability computed for the 8 am-8:15 am generic time slot of the weekday sleep pattern.

At decision block 908, based on determining that the probability of the user being currently asleep exceeds a preset threshold, the system determines that the user is currently asleep.

Figure 10:
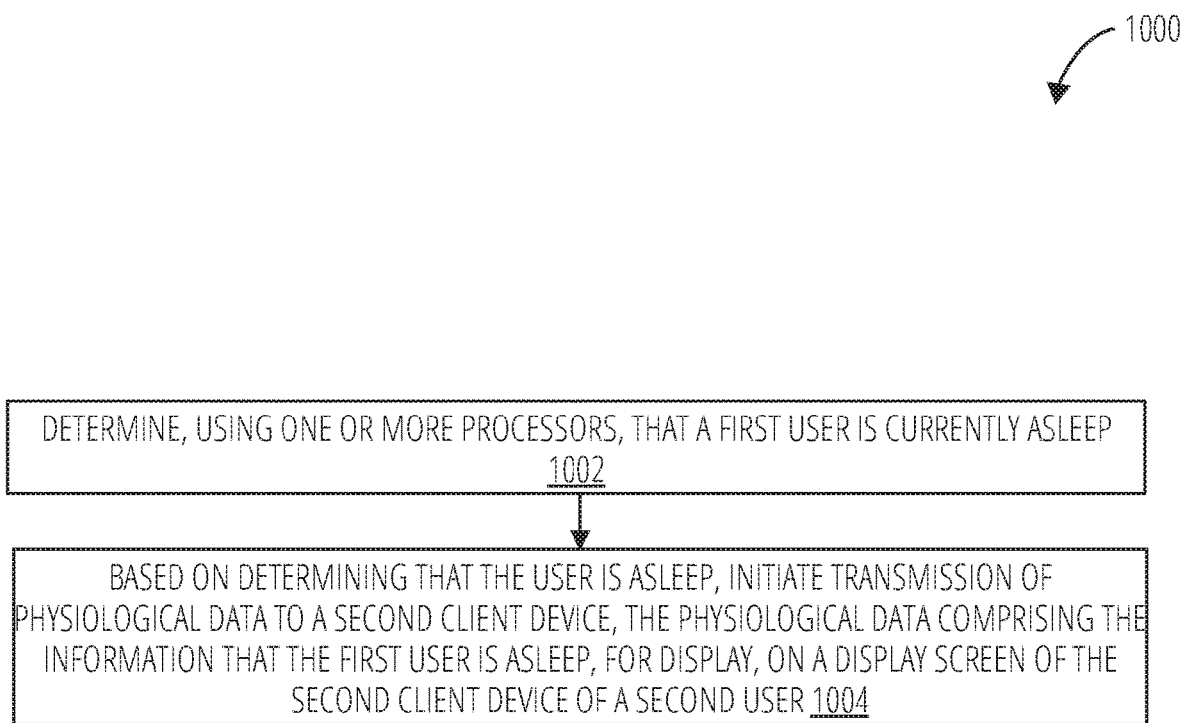
FIG. 10 illustrates a method, in accordance with one embodiment.

FIG. 10 is a flowchart illustrating a method 1000 for generating and presenting various user interfaces to share a presumed physiological state (e.g., asleep, awake) of a first user with a second user.

At block 1002, the system determines that a first user is currently asleep. In particular, the system may determine that the first user is asleep by performing the method 800 described in relation to FIG. 8.

At block 1004, based on determining that the first user is currently asleep, the system initiates transmission of physiological data to a second client device (e.g., client device 102) of the second user, the physiological data comprising the information that the first user is asleep, for display, on a display screen of the second client device. The system may cause display, on a display screen of the second client device, of a user interface (e.g., user interface 1100 of FIG. 11) including a map depicting an icon indicating a sleeping state alongside the avatar of the first user, to notify the second user that the first user is presumably asleep. In addition, if a predicted wake up time has been computed at block 814, the physiological data may further comprise the predicted wake up time, for display, on the display screen of the second client device.

Figure 11:
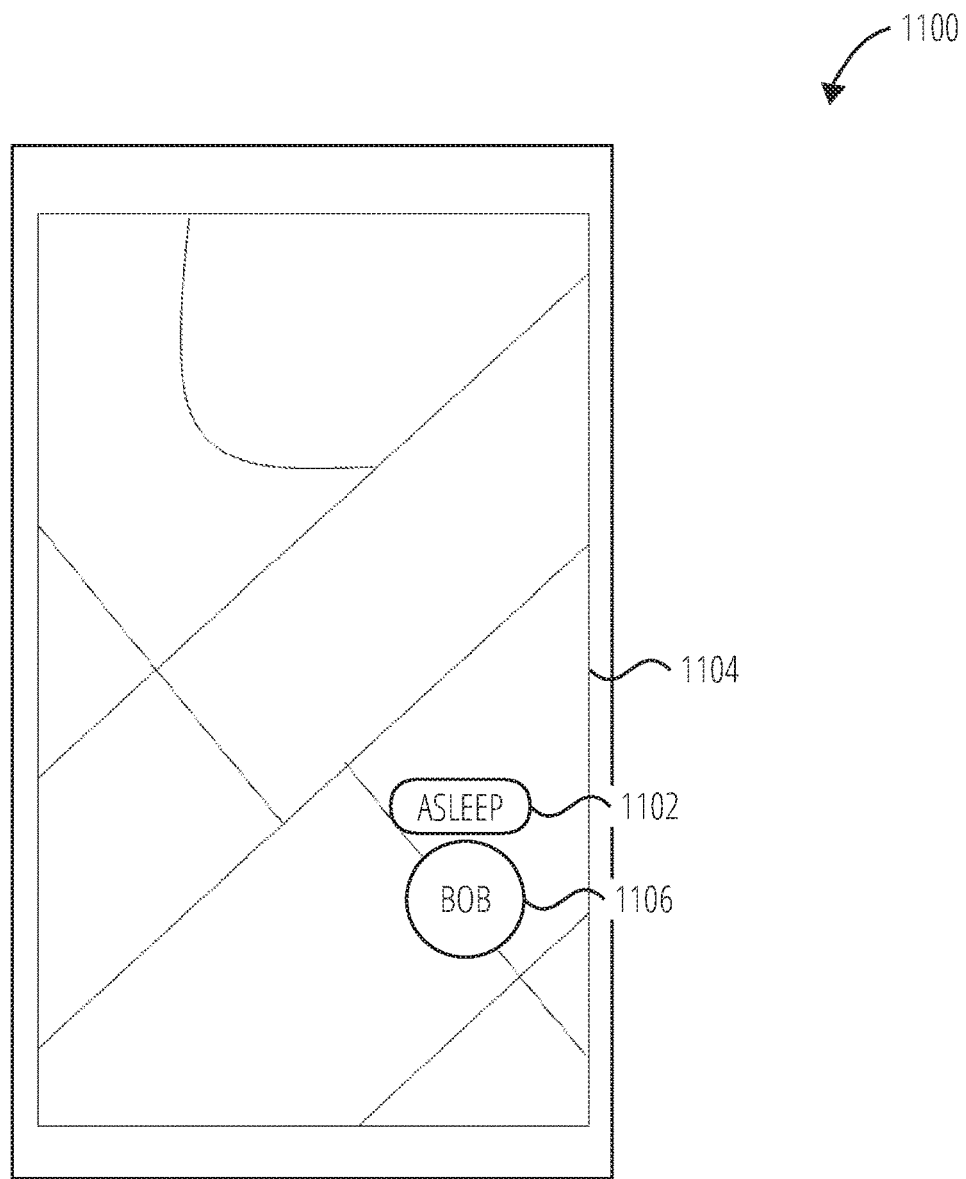
FIG. 11 illustrates a user interface, in accordance with one embodiment.

As shown in FIG. 11, user interface 1100 is an example of a user interface that may be displayed on a display screen of a second user. User interface 1100 includes a map 1104 depicting an avatar 1106 of the first user.

The avatar 1106 is a media content item associated with the first user and may include a still image, animated image, video, or other content. The avatar may include a profile picture or a default icon.

The location of the first user's avatar 1106 on the map GUI 1104 is representative of the current location of the first user. The system updates the location of the first user's avatar 1106 on the map 1104 as the location of the first user changes. If the system detects that the first user is currently asleep, the map 1104 displays an indication 1102 that the first user is asleep. The indication 1102 may be a text or an icon or a combination of both. An icon is a media content item that may include a still image, animated image, video, or other content.

The first user's avatar 1106 may be a selectable UI element triggering the display of a user interface (e.g., user interface 1200 of FIG. 12) including a map view centered on the selected avatar.

Figure 12:
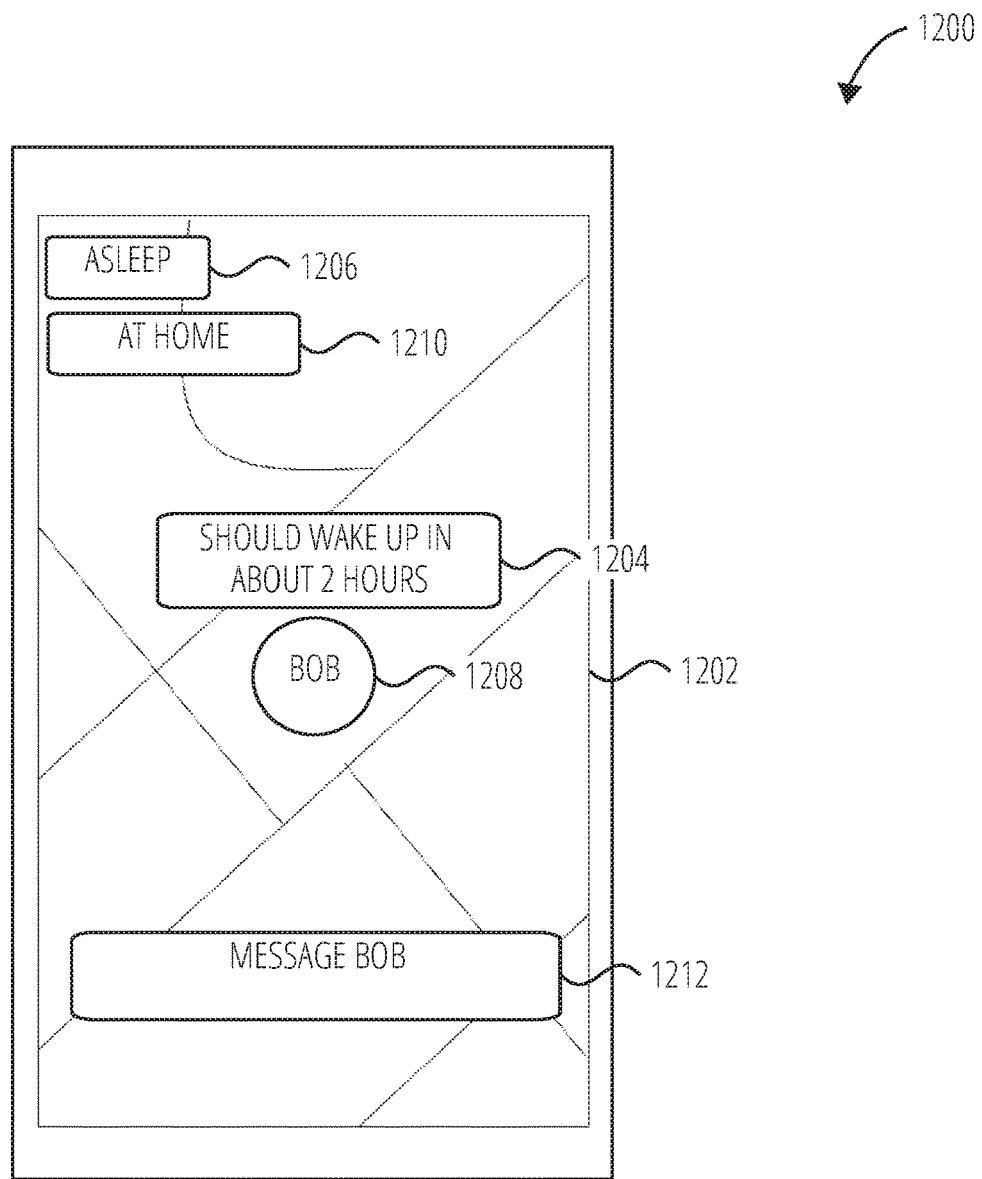
FIG. 12 illustrates a user interface, in accordance with one embodiment.

As shown in FIG. 12, UI 1200 includes a map 1202 centered around the first user's avatar 1208. The UI 1200 may also include a presumed current physiological state 1206 of the first user (e.g., asleep, awake). The UI 1200 may also include a predicted wake up time 1204 of the first user. The UI 1200 may also include a current location 1210 of the first user (e.g., at home). The UI 1200 may also include a selectable UI element 1212 for initiating or resuming a communication session with the first user via the messaging system 200. The first user's avatar 1208 may be a selectable UI element triggering the display of another UI (e.g., UI 1300 of FIG. 13).

Figure 13:
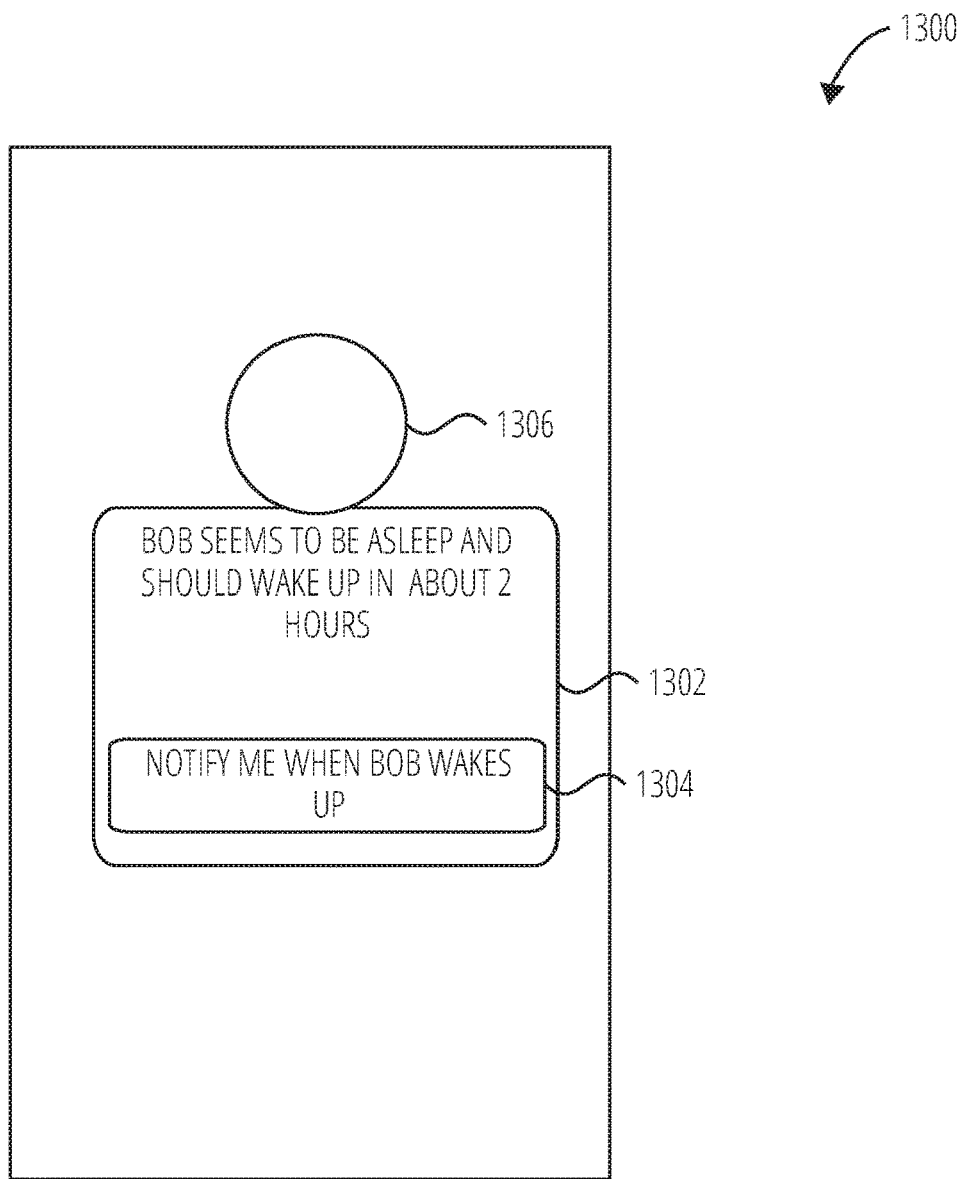
FIG. 13 illustrates a user interface, in accordance with one embodiment.

As shown in FIG. 13. UI 1300 comprises a predicted wake up time 1302. The UI 1300 may also comprise an icon 1306 indicating that the user is asleep (e.g., an icon depicting a moon or a pillow). The UI 1300 may also comprise a selectable UI element 1304 for requesting to receive a notification when the first user wakes up.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the inventive subject matter has been described with reference to specific example embodiments, various modifications and changes may be made to these embodiments without departing from the broader scope of embodiments of the present disclosure.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

As used herein, the term "or" may be construed in either an inclusive or exclusive sense. Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

"Signal Medium" refers to any intangible medium capable of storing, encoding, or carrying the instructions for execution by a machine and includes digital or analog communications signals or other intangible media to facilitate communication of software or data. The term "signal medium" shall be taken to include any form of a modulated data signal, carrier wave, and so forth. The term "modulated data signal" means a signal that has one or more of its characteristics set or changed in such a matter as to encode information in the signal. The terms "transmission medium" and "signal medium" mean the same thing and may be used interchangeably in this disclosure.

"Communication Network" refers to one or more portions of a network that may be an ad hoc network, an intranet, an extranet, a virtual private network (VPN), a local area network (LAN), a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network and the coupling may be a Code Division Multiple Access (CDMA) connection, a Global System for Mobile communications (GSM) connection, or other types of cellular or wireless coupling. In this example, the coupling may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX). Long Term Evolution (LTE) standard, others defined by various standard-setting organizations, other long-range protocols, or other data transfer technology.

"Processor" refers to any circuit or virtual circuit (a physical circuit emulated by logic executing on an actual processor) that manipulates data values according to control signals (e.g., "commands." "op codes." "machine code." etc.) and which produces corresponding output signals that are applied to operate a machine. A processor may, for example, be a CPU, a RISC processor, a CISC processor, a GPU, a DSP, an ASIC, a RFIC or any combination thereof. A processor may further be a multi-core processor having two or more independent processors (sometimes referred to as "cores") that may execute instructions contemporaneously.

"Machine-Storage Medium" refers to a single or multiple storage devices and/or media (e.g., a centralized or distributed database, and/or associated caches and servers) that store executable instructions, routines and/or data. The term shall accordingly be taken to include, but not be limited to, solid-state memories, and optical and magnetic media, including memory internal or external to processors. Specific examples of machine-storage media, computer-storage media and/or device-storage media include non-volatile memory, including by way of example semiconductor memory devices, e.g., erasable programmable read-only memory (EPROM), electrically erasable programmable read-only memory (EEPROM), FPGA, and flash memory devices; magnetic disks such as internal hard disks and removable disks; magneto-optical disks; and CD-ROM and DVD-ROM disks. The terms "machine-storage medium," "device-storage medium," and "computer-storage medium" mean the same thing and may be used interchangeably in this disclosure. The terms "machine-storage media," "computer-storage media," and "device-storage media" specifically exclude carrier waves, modulated data signals, and other such media, at least some of which are covered under the term "signal medium."

"Component" refers to a device, physical entity, or logic having boundaries defined by function or subroutine calls, branch points. APIs, or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components. A "hardware component" is a tangible unit capable of performing certain operations and may be configured or arranged in a certain physical manner. In various example embodiments, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein. A hardware component may also be implemented mechanically, electronically, or any suitable combination thereof. For example, a hardware component may include dedicated circuitry or logic that is permanently configured to perform certain operations. A hardware component may be a special-purpose processor, such as a field-programmable gate array (FPGA) or an application specific integrated circuit (ASIC). A hardware component may also include programmable logic or circuitry that is temporarily configured by software to perform certain operations. For example, a hardware component may include software executed by a general-purpose processor or other programmable processor. Once configured by such software, hardware components become specific machines (or specific components of a machine) uniquely tailored to perform the configured functions and are no longer general-purpose processors. It will be appreciated that the decision to implement a hardware component mechanically, in dedicated and permanently configured circuitry, or in temporarily configured circuitry (e.g., configured by software), may be driven by cost and time considerations. Accordingly, the phrase "hardware component" (or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware components are temporarily configured (e.g., programmed), each of the hardware components need not be configured or instantiated at any one instance in time. For example, where a hardware component comprises a general-purpose processor configured by software to become a special-purpose processor, the general-purpose processor may be configured as respectively different special-purpose processors (e.g., comprising different hardware components) at different times. Software accordingly configures a particular processor or processors, for example, to constitute a particular hardware component at one instance of time and to constitute a different hardware component at a different instance of time. Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In embodiments in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output. Hardware components may also initiate communications with input or output devices, and can operate on a resource (e.g., a collection of information). The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, "processor-implemented component" refers to a hardware component implemented using one or more processors. Similarly, the methods described herein may be at least partially processor-implemented, with a particular processor or processors being an example of hardware. For example, at least some of the operations of a method may be performed by one or more processors 1004 or processor-implemented components. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an API). The performance of certain of the operations may be distributed among the processors, not only residing within a single machine, but deployed across a number of machines. In some example embodiments, the processors or processor-implemented components may be located in a single geographic location (e.g., within a home environment, an office environment, or a server farm). In other example embodiments, the processors or processor-implemented components may be distributed across a number of geographic locations.

"Carrier Signal" refers to any intangible medium that is capable of storing, encoding, or carrying instructions for execution by the machine, and includes digital or analog communications signals or other intangible media to facilitate communication of such instructions. Instructions may be transmitted or received over a network using a transmission medium via a network interface device.

"Computer-Readable Medium" refers to both machine-storage media and transmission media. Thus, the terms include both storage devices/media and carrier waves/modulated data signals. The terms "machine-readable medium," "computer-readable medium," and "device-readable medium" mean the same thing and may be used interchangeably in this disclosure.

"Client Device" refers to any machine that interfaces to a communications network to obtain resources from one or more server systems or other client devices. A client device may be, but is not limited to, a mobile phone, desktop computer, laptop, portable digital assistants (PDAs), smartphones, tablets, ultrabooks, netbooks, laptops, multi-processor systems, microprocessor-based or programmable consumer electronics, game consoles, set-top boxes, or any other communication device that a user may use to access a network.

"Ephemeral Message" refers to a message that is accessible for a time-limited duration. An ephemeral message may be a text, an image, a video and the like. The access time for the ephemeral message may be set by the message sender. Alternatively, the access time may be a default setting or a setting specified by the recipient. Regardless of the setting technique, the message is transitory.

What is claimed is:

1. A method comprising:
   accessing, from a database coupled to a server computer, historical activity data of a user;
   extracting, using one or more processors of the server computer, historical sleep records from the historical activity data;
   clustering, by the one or more processors, the historical sleep records into a plurality of clusters;
   extracting, by the one or more processors, a sleep pattern from each one of the plurality of clusters;
   receiving, at the server computer from a client device of the user via a wireless communication over a network, an electronic communication containing current activity data of the user; and
   determining, using the one or more processors, that the user is currently asleep based on the current activity of the user and at least one of the sleep patterns.

2. The method of claim 1, wherein determining, using the one or more processors, that the user is currently asleep comprises:
   determining that the current activity data of the user verifies a set of criteria;
   selecting one of the plurality of sleep patterns based on the current activity of the user;
   computing a probability of the user being currently asleep based on the selected sleep pattern; and
   wherein the user is determined to be currently asleep based on the computed probability exceeding a threshold.

3. The method of claim 2, further comprising computing a predicted wake up time based on the selected sleep pattern.

4. The method of claim 2, wherein each historical sleep record comprises an historical timetable comprising a plurality of historical time slots, each historical time slot being associated with a probability of the user being asleep during said historical time slot, the probability of the user being asleep during said historical time slot being computed based on the historical activity data verifying the set of criteria for said historical time slot.

5. The method of claim 4, wherein each one of the sleep patterns comprises a generic timetable comprising a plurality of generic time slots, each generic time slot being associated with a probability of the user being asleep during said generic time slot; and
   wherein extracting a sleep pattern from one of the plurality of clusters comprises:
   for each generic time slot:
   retrieving, from the historical sleep records included in the cluster, one or more probabilities of the user being asleep during one or more historical time slots matching said generic time slot; and
   computing a probability of the user being asleep during said generic time slot, the probability of the user being asleep during said generic time slot being computed based on the one or more probabilities of the user being asleep during the one or more historical time slots matching said generic time slot.

6. The method of claim 2, wherein the set of criteria includes that the client device is static.

7. The method of claim 2, wherein the set of criteria includes that no user input has been detected at the client device for a preset period of time.

8. The method of claim 2, wherein the set of criteria includes that a location of the user is not within a preset distance of the location of a second user.

9. The method of claim 2, wherein the set of criteria includes that a location of the user is within a preset distance of the location of a domicile of the user.

10. The method of claim 1, wherein each historical sleep record is associated with one of a plurality of categories; and
    wherein clustering the historical sleep records into a plurality of clusters comprises grouping together the historical sleep records associated with one of the categories.

11. The method of claim 10, wherein the categories are days of a week.

12. The method of claim 1, further comprising:
    based on determining that the user is currently asleep, initiating transmission of physiological data to a second client device of a second user, the physiological data comprising the information that the first user is sleeping for display on a display screen of the second client device.

13. The method of claim 12, wherein initiating transmission of physiological data to a second client device of a second user includes attaching the physiological data to an ephemeral message accessible for a predetermined duration of time; and
    wherein display on a display screen of the second client device includes:
    receiving a request from the second client device to access the ephemeral message;
    in response to the request, causing the ephemeral message to be displayed on the second client device; and
    ceasing display of, and access to, the ephemeral message in response to expiration of the predetermined duration of time.

14. A system comprising:
    one or more processors; and
    a memory storing instructions that, when executed by the one or more processors, configure the system to perform operations comprising:
    accessing, from a database coupled to the processor, historical activity data of a user;
    extracting, using the one or more processors, historical sleep records from the historical activity data;
    clustering the historical sleep records into a plurality of clusters;
    extracting a sleep pattern from each one of the plurality of clusters;
    receiving, from a client device of the user, via a wireless communication over a network, an electronic communication containing current activity data of the user; and
    determining, using the one or more processors, that the user is currently asleep based on the current activity of the user and at least one of the sleep patterns.

15. The system of claim 14, wherein determining that the user is currently asleep comprises:
    determining that the current activity data of the user verifies a set of criteria;
    selecting one of the plurality of sleep patterns based on the current activity of the user;

computing a probability of the user being currently asleep based on the selected sleep pattern; and wherein the user is determined to be currently asleep based on the computed probability exceeding a threshold.

16. The system of claim 15, wherein the operations further comprise:

computing a predicted wake up time based on the selected sleep pattern.

17. The system of claim 15, wherein the set of criteria includes one or more of the following criteria:

the client device is static;

no user input has been detected at the client device for a preset period of time;

a location of the user is not within a preset distance of the location of a second user; and the location of the user is within a preset distance of the location of a domicile of the user.

18. The system of claim 14, wherein the operations further comprise:

based on determining that the user is currently asleep, initiating transmission of physiological data to a second client device, the physiological data comprising the information that the first user is sleeping for display on a display screen of the second client device of a second user.

19. The system of claim 18, wherein initiating transmission of physiological data to a second client device of a second user includes attaching the physiological data to an ephemeral message accessible for a predetermined duration of time; and wherein display on a display screen of the second client device includes:

receiving a request from the second client device to access the ephemeral message;

in response to the request, causing the ephemeral message to be displayed on the second client device; and ceasing display of, and access to, the ephemeral message in response to expiration of the predetermined duration of time.

20. A non-transitory computer-readable storage medium, the computer-readable storage medium including instructions that, when executed by a computer, cause the computer to perform operations comprising:

accessing, from a database coupled to a server computer, historical activity data of the user;

extracting, using one or more processors of the server computer, historical sleep records from the historical activity data;

clustering the historical sleep records into a plurality of clusters;

extracting a sleep pattern from each one of the plurality of clusters;

receiving, at the server computer, from a client device of the user, via a wireless communication over a network, an electronic communication containing current activity data of the user; and determining, using the one or more processors, that the user is currently asleep based on the current activity of the user and at least one of the sleep patterns.

* * * * *